(12) United States Patent
Erb et al.

(10) Patent No.: US 6,300,082 B1
(45) Date of Patent: Oct. 9, 2001

(54) METHOD AND APPARATUS FOR MEASUREMENT OF THE EFFECT OF TEST COMPOUNDS ON SIGNAL TRANSDUCTION AT THE LEVEL OF BIOLOGICAL RECEPTORS

(75) Inventors: Judith L. Erb; James G. Downward, IV; John R. Erb-Downward, all of Ann Arbor, MI (US); James L. Wittliff, Louisville, KY (US)

(73) Assignee: IA, Inc., Ann Arbor, MI (US)

( * ) Notice: Subject to any disclaimer, the term of this patent is extended or adjusted under 35 U.S.C. 154(b) by 0 days.

(21) Appl. No.: 09/045,224

(22) Filed: Mar. 20, 1998

(51) Int. Cl.[7] .................................................. G01N 33/543
(52) U.S. Cl. .......................... 435/7.1; 385/12; 385/123; 385/129; 422/55; 422/82.05; 422/82.08; 422/82.11; 435/7.9; 435/287.1; 435/287.2; 435/288.7; 435/808; 436/65; 436/164; 436/165; 436/172; 436/510; 436/518; 436/527; 436/805; 436/814; 436/811; 436/815; 436/817
(58) Field of Search ............................. 385/12, 123, 129; 422/55, 82.05, 82.08, 82.11; 435/7.9, 7.1, 287.1, 287.2, 288.7, 808; 436/518, 527, 510, 65, 164, 165, 805, 814, 811, 815, 817, 172

(56) References Cited

U.S. PATENT DOCUMENTS

| 4,558,014 | * | 12/1985 | Hirschfeld et al. | ................. | 436/527 |
| 4,608,344 | * | 8/1986 | Carter et al. | ........................... | 436/34 |
| 4,671,938 | * | 6/1987 | Cook | ...................................... | 422/57 |

(List continued on next page.)

OTHER PUBLICATIONS

Maggio et al, "Enzyme Immunoassay", CRC Press Inc., Boca Raton, Florida, 1980, p. 173.*

Primary Examiner—Christopher L. Chin
(74) Attorney, Agent, or Firm—Kohn & Associates

(57) ABSTRACT

A method and apparatus for measuring binding between a plurality of molecules of a biological receptor protein and a plurality of molecules of a type which binds to said biological receptor is presented. Apparatus utilizes a sensor possessing a waveguide to which have been attached in close proximity to its surface, features resembling molecules having binding affinity for said biological receptor. Light is injected into said waveguide so as to produce an evanescent field at its surface. Molecules of receptor protein are tagged with a tag belonging to that class of chemicals which alters a characteristic of light, when said light passes through said chemical tag. Apparatus utilizes a rapid means of monitoring the change in optical signal coming from the waveguide as binding proceeds between tagged receptor protein and the binding molecular feature of the waveguide. This allows direct measurement of binding and dissociation rates between the receptor and the binding feature of the waveguide. By using a waveguide having a feature resembling a ligand for the receptor, the potential hormonal activity of a test substance may be evaluated from its ability to compete with the waveguide for binding with the receptor. The effect of a test compound on binding of receptor protein to a subsequent element in a hormonal signal transduction mechanism is evaluated by measuring the impact of the test compound on binding between receptor protein and a feature resembling said next element of the signal transduction mechanism. Methods are provided whereby such data may be used to compute affinity constants, binding activity, complex affinity constants resulting from cooperativity, and kinetic parameters for the receptor and test ligand and for the receptor and the next element of the signal transduction mechanism. Preferred embodiments of the invention illustrate application of the method and apparatus to measuring binding between biological receptors and their nuclear response elements, and the use of this type of measurement for assessment of the activity of estrogen mimics present in a test sample, and for evaluation of pharmaceuticals intended to treat hormone dependent cancers.

20 Claims, 7 Drawing Sheets

U.S. PATENT DOCUMENTS 4,775,637 * 10/1988 Sutherland et al. .................. 436/527
4,810,658 *  3/1989 Shanks et al. ........................ 436/172
4,818,710 *  4/1989 Sutherland et al. .................. 436/527
4,978,503 * 12/1990 Shanks et al. .......................... 422/58
5,082,630 *  1/1992 Partin et al. ............................ 422/83
5,663,054 *  9/1997 Williams et al. .................... 435/7.93

* cited by examiner

SEQUENCE LISTING

<160> NUMBER OF SEQ ID NOS: 2

<210> SEQ ID NO 1
<211> LENGTH: 35
<212> TYPE: DNA
<213> ORGANISM: Artificial Sequence
<220> FEATURE:

-continued

```
<223> OTHER INFORMATION: Description of Artificial Sequence: binds human
      estrogen receptor protein

<400> SEQUENCE: 1
gtccaaagtc aggtcacagt gacctgatca aagtt                              35

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: binds human
      estrogen receptor protein

<400> SEQUENCE: 2
caggtttcag tccagtgtca ctggactagt ttcaa                              35
```

METHOD AND APPARATUS FOR MEASUREMENT OF THE EFFECT OF TEST COMPOUNDS ON SIGNAL TRANSDUCTION AT THE LEVEL OF BIOLOGICAL RECEPTORS

GRANT INFORMATION

This invention was made with government support under grants ES07471 and ES10076 awarded by the National Institute of Health. The government has certain rights in the invention.

BACKGROUND OF THE INVENTION

1. Field of the Invention

This invention relates to an apparatus and a methodology for measurement of the effect of certain test compounds, such as and without limitation, hormone mimics, on biological signal transduction at the level of biological receptors and their binding to subsequent molecules such as and without limitation DNA molecules, involved in the transduction mechanism. The word "receptor" is defined for purpose of this invention according to the definition appearing in *Illustrated Dictionary of Immunology*, edited by Julius M. Cruse and Robert E. Lewis and published by CRC Press, Boca Raton, 1995, p.258, ISBN 0-8493-4557-X: "A molecular configuration on a cell or macromolecule that combines with molecules that are complementary to it."

In one embodiment the apparatus and methodology utilizing the principles of the invention are adapted for use as a screening tool for recognizing the presence of estrogen mimics in a sample. In a second embodiment the apparatus and methodology utilizing the principles of the invention are adapted for use as a method for measuring estrogen receptor content in a tissue biopsy sample and evaluating in vitro the probable response of cancer cells, of a type present in that tissue biopsy sample, to certain pharmacologic agents which act through receptor binding. The fiber optic biosensor described herein provides information which reflects the biological impact of the sample. It also has the potential for elucidating mechanisms of receptor action in that the sensor provides a means of obtaining kinetic information on receptor binding events as the binding process occurs.

2. Background of the Invention

Many biological processes are regulated by the binding of regulatory molecules such as hormones, neurotransmitters or cytokines to specific biological receptor molecules. Upon binding to the regulatory molecule, the receptor activates the next step in a signal transduction mechanism by itself binding to another molecular component of the transduction mechanism such as a nuclear response element. The affinity with which this second stage of receptor binding occurs, or in some cases, whether or not this second stage binding occurs at all, is affected by the binding of the regulatory molecule to the receptor. A review of such mechanisms can be found in an article entitled "Mechanisms of Signal Transduction: Sex Hormones, Their Receptors and Clinical Utility" by James L. Wittliff and Wolfgang Raffelsberger, which appeared in *Journal of Clinical Ligand Assay*, Volume 18, Number 4, Winter, 1995. This text is fully and completely incorporated herein by reference, word for word and paragraph for paragraph.

There are many benefits which derive from the study of both the binding of receptors to regulatory molecules and the second stage binding of the receptors to another component of the signal transduction mechanism. Such study can assist in the design of drugs which exert their biological effect through binding to biological receptors. It can also lead to recognition of compounds in the environment which have the capacity to disrupt important biological regulatory mechanisms by virtue of the ability of such molecules to bind to molecular receptors. It is believed that the presence of such molecules in the environment plays a role in the development of a variety of disease types including cancer, and reproductive problems.

Current methods used for studying these binding phenomena are described in the previously cited review. Because the methods require physical separation of bound from unbound molecules, the methods are quite time consuming and do not have the capacity to provide real time data while binding is occurring between a receptor and a regulatory molecule or between receptors and another component of the signal transduction mechanism. The reliance of current methods on radiolabeled ligands also limits the circumstances under which such measurements can be made.

Evanescent fiber optic sensors provide a method whereby a plurality of molecules of interest bearing an optical tag can be directly monitored as they bind to binding partners attached to an optical fiber. An optical tag may comprise molecules belonging to that class of chemicals which interact with light in a manner so as to alter a characteristic of light received from said sensor by means such as and without limitation, absorbance, fluorescence, luminescence, or polarization; or which produces a second chemical which interacts with light in said manner, such as and without limitation, an enzyme having action producing or destroying a fluorescent, absorbing, luminescent or polarizing compound. The molecular tag may be chemically attached to said plurality of molecules or it may be chemically attached to a plurality of a second type of molecule such as and without limitation, an antibody, having affinity for said molecule of biological interest. Light traveling through an optical fiber at or near the critical angle is totally internally reflected so that it does not significantly effect unbound tagged molecules in the surrounding solution. Total internal reflection does, however, produce an evanescent field which extends about 1000 angstroms from the surface of the fiber. This means that a response from molecules bound to the surface of the fiber can be excited by light totally internally reflected within the fiber, without exciting a response from unbound molecules in the surrounding solution. Therefore measurement of binding can be made without the necessity for physical separation of bound from unbound molecules. Evanescent sensors which measure concentrations of antigen in a solution based upon measurement at a certain time of an amount of fluorescent antigen in the sample which is bound to antibodies on the fiber. Such sensors have been reported in literature and are thoroughly described in the book *Biosensors with Fiber Optics*, Donald L. Wise and Lemuel B. Wingard, Jr. Editors; Humana Press, Clifton, N.J., 1991. This text is fully and completely incorporated herein by reference, word for word and paragraph for paragraph.

The use of an evanescent sensor having the membrane receptor for acetyl choline bound to its surface to explore the binding of cholinergic ligands has been previously reported by Kim B. Rogers, J. J. Valdes, and Mohyee E. Elderfrawi in an article entitled *Acetylcholine receptor fiberoptic evanescent fluorosensor*, appearing in the Nov. 1, 1989 issue of Analytical Biochemistry, 182(2):353–9. Membrane receptors for neurotransmitters function differently than receptors for hormones in that membrane receptors do not utilize subsequent binding to a nuclear response element in signal transduction. The transduction process for membrane receptors involves subsequent alteration in transport of ions through channels in the membrane. Use of hormone receptors as reagents in conjunction with an evanescent sensing apparatus possessing a feature resembling a nuclear response element for said hormone receptor has not, to our knowledge, been previously described.

3. Background of the Estrogen Receptor Embodiment

A general background is provided which pertains to the specific embodiment employing the estrogen receptor and the estrogen response element as a means of testing compounds for estrogenic or anti-estrogenic activity. This embodiment is described for the specific application of identification of environmental estrogen mimics and for the specific application of in vitro assessment of the probable efficacy of specific anti-estrogenic compounds, such as and without limitation, tamoxifen, in the treatment of cancer.

The Problems Posed by Estrogen Mimics

During the past 50 years there. has been a marked increase in the number of abnormalities relating to the human reproductive system. Endometriosis, once thought to be a rare condition, has become the most common diagnostic entity in gynecology today. The incidence of female breast cancer is now 1 in 8. A retrospective analysis of data since the 1940's revealed that the sperm count of men all over the world has dropped by 50%, 3 while at the same time testicular cancer rates have tripled and prostate cancer rates have doubled. Furthermore, a 1991 issue of Time magazine reported that one million couples seek treatment for infertility in this country each year. While the above mentioned conditions may seem separate and unrelated, the evidence is that there is one common thread that runs throughout them all: Estrogen Mimics. The evidence warranting concern proved sufficient to cause Congress to pass legislation mandating the EPA to establish a method for evaluating the impact of estrogen mimics in environmental samples.

Current Methods for Measuring the Estrogenic Potency of a Sample

The relationship between the reproductive alterations in humans and the presence of environmental pseudo-estrogens, is difficult to assess because of methodological complexity. One difficulty is that a wide variety of apparently structurally unrelated substances act as estrogen mimics. This makes performing measurements of estrogen mimicry for each possible individual chemical unreasonably time consuming. Additionally, as yet unidentified estrogen mimics which might be present in a sample, could not be measured by chemical or immunologic methods because such methods require knowledge of the identity of the analyte. Although bioassay methods are useful to identify the relative estrogenic activity of pseudo-estrogens, performing bioassays is generally time-inefficient, tedious, and costly.

Because the hER protein is the biological transducer for the first step of estrogen activity, namely binding between the estrogen and the receptor, it possesses the ideal ligand specificity to recognize all estrogenic compounds. This, together with its high affinity (i.e., sensitivity of recognizing small ligand concentrations) make it an ideal probe to combine with biosensor technology.

The Relationship Between Estrogen Receptor and Effective Cancer Treatment

The observation that only 10% of estrogen-receptor negative breast cancer tumors respond to endocrine therapy while 60% of the estrogen-receptor positive tumors respond has made the assessment of estrogen-receptor content of tumors an extremely valuable aid in planning therapeutic course of treatment for breast cancer. Although positive assay for both estrogen-receptor and progesterone receptor increases the likelihood of a positive response to anti-estrogen therapy, still 30–40% of estrogen-receptor positive tumors do not respond to endocrine therapy. A method which will provide improved in vitro assessment of tumor response to endocrine therapy will be of great value in that those patients who require more severe forms of chemotherapy or radiation treatment will receive such treatments initially rather than after endocrine therapy has failed.

Binding between a receptor and its nuclear response element leads to transcription of m-RNA and subsequent protein synthesis. The success of using tamoxifen to treat many ER positive breast cancers illustrates the benefits of targeting molecules involved in these mechanisms of signal transduction and transcriptional regulation.

The Role of Er and Ere in the Biological Response to Estrogens

The initial biological event in estrogen stimulation involves binding of the estrogen or estrogen mimic to the steroid binding region of the receptor.

In a system unchallenged by non-endogenous estrogens, estrogen binds to the estrogen receptor inducing a conformational change that allows for tight binding of the receptor to its recognition element, the ERE, on the DNA. When bound to the DNA this conformation allows for the recruitment of other macromolecules (coactivators, polymerases, kinases, etc.) which, when bound to promoter and TATA regions, incite the transcription of the gene under estrogen dependent regulation. The mRNA is then translated into the proteins responsible for the phenomena which are measured by bioassays.

When non-endogenous estrogens are introduced, the story becomes more varied and much more complex. Many compounds bind to the ER, however, not all are capable of inducing the conformational changes that allow for optimal DNA binding. Those that can bind the receptor to the DNA with a tight affinity introduce an additional wrinkle in that the bound receptor may not be in the proper conformation to recruit the necessary transcription factors. These tightly bound but inactive receptors are occupying many of the ERE binding sites, preventing proper transcription from occurring. This complexity cannot be probed by any single assay that relies on the initiation of transcription for its determination of estrogenisity.

Understanding the Instrument Being Utilized

The preferred embodiments of this invention utilize the estrogen receptor (ER) and the estrogen response element (ERE) as the recognition elements in an evanescent fiber-optic sensor to produce an instrument for measuring the potential of chemicals, environmental contaminants, and pharmaceuticals to interfere with estrogen mediated biological processes. Understanding of the instrument requires an understanding of (1) the principle of operation of evanescent fiber optic sensors and (2) the role of these two molecules in estrogen mediated biological responses.

The Principle of Operation of Evanescent Sensors

The essential feature of an evanescent biosensor, is confinement of the measurement area to the surface of the waveguide by taking advantage of the evanescent field associated with total internal reflection within the fiber. This was originally described in the context of immunoassay by Tomas Hirshfield in U.S. Pat. No. 4,447,546 entitled "Fluorescent immunoassay employing optical fiber in a capillary tube" which is herein incorporated by reference, line by line and word for word. The manner in which this functions is as follows.

Consider light incident at angle q on the boundary between two optical media with indexes of refraction N and n (N>n). When the light is incident on the boundary at angles greater than or equal to the critical angle, $\theta_{crit}$ where $\sin(\theta_{crit})=n/N$, the light will be totally reflected from the surface. Although, light is not transmitted past the boundary and into the media with the lower index of refraction, electromagnetic theory shows that an evanescent electromagnetic field decays exponentially with perpendicular distance from the boundary. The characteristic 1/e depth of this decay for light of wavelength $\lambda$ incident at angle $\theta$ is given by the equation:

$$(\lambda 4\pi)(N^2 \sin^2\theta - n^2)^{-\frac{1}{2}}. \quad \text{Equation 1}$$

This distance is large compared with the dimensions of proteins and biologically significant nucleotides. Thus, the light with wavelength $\lambda_1$ will interact with fluorescent molecules, which are associated with any proteins or nucleotides that are attached near the probe's surface, to generate fluorescence at wavelength $\lambda_2$. Because the waveguide is very large compared with the size of the proteins or nucleotides, a large fraction of the emitted fluorescence light at wavelength $\lambda_2$ will intersect the fiber optic sensor, then be trapped inside due to total internal reflection, and finally be carried back to a solid state light detector in the control unit.

SUMMARY OF THE INVENTION

It is a first object of the present invention to provide a method and apparatus for utilizing biological receptors as reagents for identification of compounds having potential for producing disruption of a biological regulatory system, including and without limitation the reproductive system, and other endocrine systems. In this context, the word "mimic" is used to describe a compound which binds to the biological receptor for a certain biological regulatory molecule such as and without limitation, estrogen, progesterone and is not chemically identical to said biological regulatory molecule.

It is a second object of the present invention to provide a method and apparatus for evaluating the presence or absence of estrogen mimics in an aqueous sample.

It is a third object of the present invention to provide a method and apparatus for evaluating the presence or absence of progesterone mimics in an aqueous sample.

It is a fourth object of the present invention to provide a method and apparatus for evaluating the presence or absence of testosterone mimics in an aqueous sample.

It is a fifth object of the present invention to provide a method and apparatus for measuring the binding of certain compounds to biological receptor molecules which overcomes the various disadvantages of the prior art.

It is a sixth object of the present invention to provide a method for measuring the binding of biological receptor molecules to other molecular components which comprise a biological signal transduction mechanism.

It is a seventh object of the present invention to provide a method for measuring the impact of certain compounds on the binding of biological receptor molecules to other molecular components which comprise a biological signal transduction mechanism.

It is an eighth object of the present invention to provide a method which goes beyond the prior art in that it provides real time description of binding between biological receptors and their ligands.

It is a ninth object of the present invention to provide a method which goes beyond the prior art in that it provides real time data on binding between biological receptors and other molecular components which comprise a biological signal transduction mechanism.

It is a tenth object of the present invention to provide a method and apparatus for evaluation of potential for certain compounds to act as chemotherapeutic agents for treatment of hormone dependent cancers.

It is an eleventh object of the present invention to provide a method and apparatus for assessing the type of impact (such as inhibitory impact or excitatory impact) on biological regulatory systems a certain compound will be likely to exert.

It is a twelfth object of the present invention to provide a method and apparatus for assaying the amount of a particular receptor, such as and without limitation estrogen receptor, progesterone receptor and testosterone receptor present in tissue biopsy, which goes beyond prior art in providing a rapid and simple means of identifying both active and inactive receptor.

What has not been previously reported and what constitutes the innovation of this invention is description of an apparatus and method for the use of tagged receptor in conjunction with either or both of two types of optical fibers: one having a plurality of a regulatory molecule for the receptor bound to its surface and the other having a plurality of another component of the signal transduction mechanism such as and without limitation, the nucleotide sequence of the binding region of a response element to which the receptor binds. This combination of components permits assessment of both the affinity of a test compound for the receptor relative to the receptor's affinity for the regulatory molecule on the fiber and assessment of the impact which binding of the test molecules by receptors has on the subsequent binding of receptors to a molecular component of the signal transduction mechanism. These two pieces of information taken together provide a useful indication of the likely biological impact a test compound will have.

The instrument herein described allows quick and easy determination of the danger posed by such compounds through the utilization of a fiber optic probe that can tell 1) if the compound is binding to the Estrogen Receptor and 2) what impact the compound is having on the binding of the receptor to the DNA response element.

Our fiber optic sensor utilizes human estrogen receptor (hER) which has been cloned and over expressed in yeast in a manner similar to that described for expression in *Escherichia coli* as described by J. L. Wittliff, J. Dong, C. Schaupp, Z. Nawaz and T. R. Butt on pages 22016–22022 of the Dec. 15, 1190 issue of *The Journal of Biological Chemistry* in an article entitled "Expression and Characterization of an Active Human Estrogen Receptor as a Ubiquitin Fusion Protein from *Escherichia coli*," which is hereby incorporated into this document line by line and word for word. Unlike the estrogen receptor present in tissue sections or homogenates, which are highly labile, the yeast expressed receptor is stable. The sensor also utilizes a double stranded nucleotide having the base sequence present in the ERE. These biological recognition elements have been combined with an evanescent fiber-optic sensor. Such sensors typically provide measurements in 3–10 minutes and in our experience respond to femtomoles of receptor. This is well within the desirable detection limits for estrogens and their mimics in environmental samples as well as for assay of estrogen receptor activity in tissue biopsies.

The sensor described in the first example of a preferred embodiment has two parts. In the first the hER and estrone-3 glucuronide are two partners of a binding pair. E1-g is coupled to an optical fiber and the hER is fluorophore tagged. The optical fiber is mounted in a capillary tube and a mixture of sample and fluorophore-tagged hER is presented to the fiber for binding. In the case where the source of the hER is a biological sample to be tested, it is often most convenient to achieve fluorophore tagging of the hER by means of affinity binding to a fluorophore tagged anti-ER antibody. Fiber fluorescence is read using an evanescent sensing instrument. Within the evanescent field on the fiber surface, hER fluoresces when stimulated by light traveling through the fiber. If compounds which bind to the hER are present in the sample, they will compete for estrogen-binding sites on the receptor thereby altering binding to the E1-g on the fiber. This appears as a change in fluorescent response.

In the second part of the sensor, a fiber having the ERE coupled to its surface reports binding of the fluorescent estrogen-receptor complex by a similar mechanism. If estrogen agonists are present, fluorescence on the ERE-fiber is increased because the complex formed with the hER facilitates binding between the hER and the ERE. If estrogen antagonists are present, their complex with the hER will not as effectively facilitate binding between the hER and the ERE and the fluorescent response of the ERE-fiber will not increase as significantly as it did in the absence of the test sample. The combined information from the two fibers is expected to indicate whether the compound being tested would (1) stimulate an estrogenic biological response, (2) suppress estrogenic responses or (3) not affect estrogenic response.

A second example of a preferred embodiment of the invention also incorporates a fiber having anti-receptor antibody covalently attached to its surface for the purpose of comparing direct immunoassay of the estrogen receptor in tissue biopsy with assay by means of binding to an ERE fiber.

The use of the fiber-optic technology allows the instrument to be rugged, compact and portable, while simultaneously providing sensitive, fast and accurate results. The instrument being developed will provide a simple screening method with rapid response which can replace time-consuming bioassay methods and greatly expedite efforts to determine the magnitude of the threat posed by environmental pollutants with estrogenic mimicry. It will also provide a simple means of compliance with legislation requiring monitoring and control of estrogenic compounds released into the environment The invention is described in detail for examples of the preferred embodiments which utilize fluorescent-tagged estrogen receptor in conjunction with a fiber which is coupled to estrone-3-glucuronide and/or another which is coupled to the nucleotide sequence of the nuclear estrogen response element, and/or another which is coupled to an antibody to some epitope on the receptor. The estrogen receptor may be tagged either directly through chemical coupling to fluorophore molecules, or indirectly through affinity interaction with a second molecule, such as and without limitation, an antibody to the receptor, which has been tagged with a fluorophore. This combination of components provides a useful tool for (1) recognizing the presence of estrogen mimics in aqueous samples of environmental interest and for predicting whether the mimic is likely to exert an enhanced estrogenic effect in vivo or act to reduce the estrogenic impact of endogenous estrogens; (2) evaluating compounds such as and without limitation, tamoxifen, which might be useful in treatment of hormone dependent cancers; (3) measuring the amount of estrogen receptor present in tumor biopsies; and (4) identifying the presence of mutated or abnormal estrogen receptor in tumor biopsies.

DESCRIPTION OF FIGURES

Fuller understanding of apparatus used in the examples of preferred embodiments of the invention is obtained by reference to the following detailed description taken in connection with the accompanying drawings in which like numerals in said drawings denote like parts, and wherein.

DETAILED DESCRIPTION OF PREFERRED EMBODIMENTS OF THE METHOD OF THE INVENTION

Figure 1:
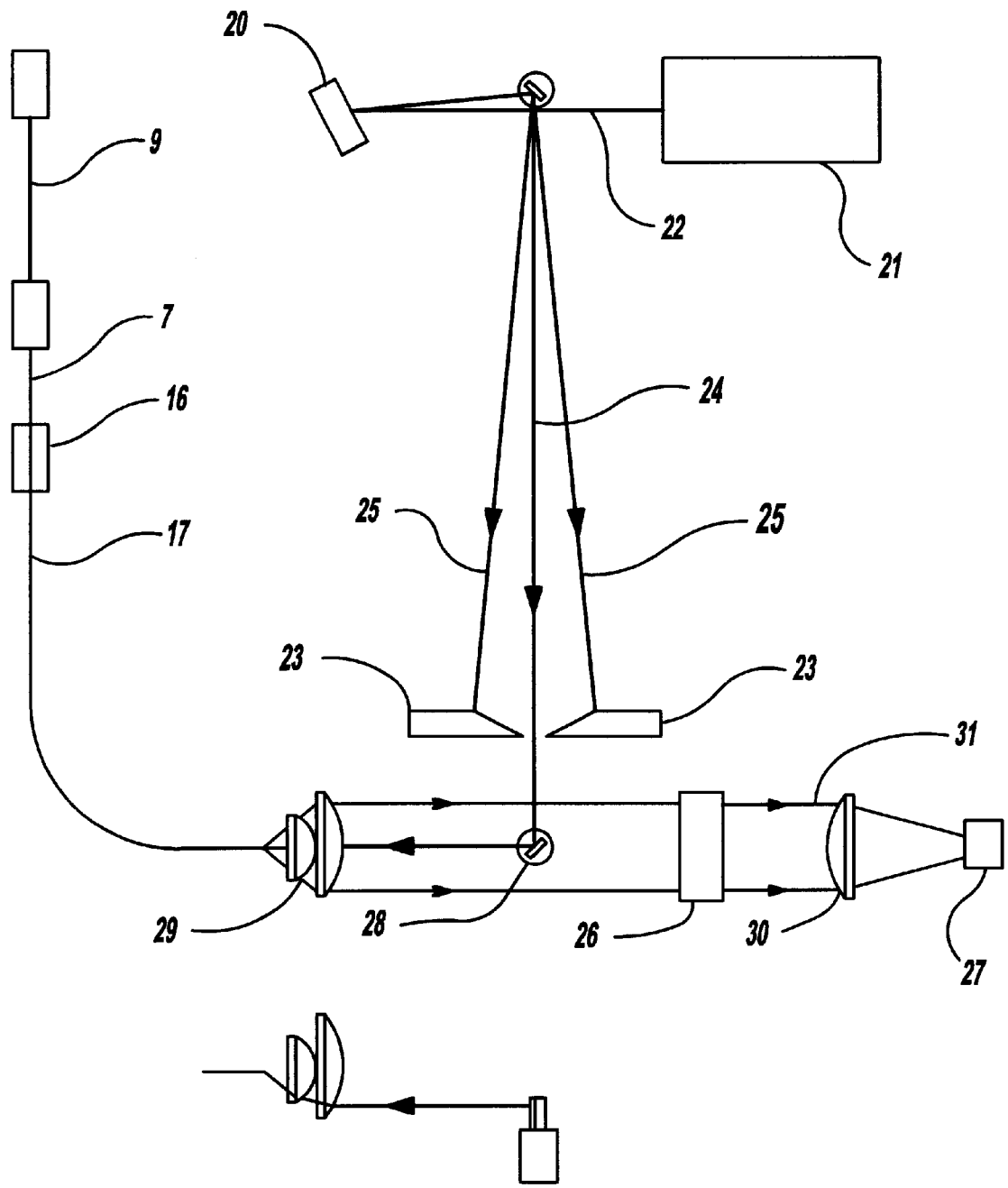
FIG. 1: Shows top and side views of the idealized optical apparatus of the invention, said apparatus having means for removing side bands from a laser source.

General Apparatus and Methods of all Preferred Embodiments

Direct real time observation of binding between a certain nucleotide sequence and a certain biological receptor is not currently part of the prior art of molecular biology or biochemistry. Binding between such molecules in typically measured by radiobinding assays requiring separation of bound from unbound components. The following general method is provided whereby an evanescent sensing fluorometry apparatus such as and without limitation, the one which has been described in FIGS. 1–6, may be used to provide direct real time observation of binding between a certain nucleotide sequence and a certain biological receptor.

Although all specific examples of preferred embodiments of the present inventions utilized evanescent fiber optic sensors of the type described in FIGS. 1–6, it is easy to visualize the possibility that the applications described in the objects of the present invention could be carried out using other evanescent sensing apparatus such as and without limitation fiber optic sensors of other designs evanescent sensors utilizing waveguides of other geometries, such as a planar waveguide. All such applications of evanescent sensing instruments are considered to be within the objects and scope of the objects of the present invention. The apparatus and methods of the objects of the present invention are described in the most general case as being comprised of the following elements. Those elements having numbers ending in a (for apparatus) comprise the components of the apparatus of the present invention. Those elements having numbers ending in m (for method) comprise the steps of the method of the present invention.

1a: A quantity of optical waveguide pieces the number of which are determined by the number of sensors which are to be created, which have been cut to the size required from longer length of optical waveguide, and having been subsequently first processed together to create clean bare surfaces or clean bare surface regions interspersed with a controlled surface density of hydrophobic islands, and then having been treated so as to attach, directly or indirectly to the waveguide surface, a plurality of molecules or polymers which includes structural features conferring upon said molecules or polymers a binding affinity for a certain molecule of biological interest, are processed to create the sensors. This linkage may be accomplished either by adsorption of said molecules or polymers onto said exposed surface or by chemical reaction with a series of chemicals resulting in covalent bonding of said molecules or polymers to the exposed waveguide surface or by entrapment of said molecules within a polymer or gel matrix surrounding said optical waveguide.

2a: An optical apparatus which injects into said optical waveguide of component (1a), light at or near the critical angle for said waveguide in the sample medium, and measures the fluorescence, absorbance, luminescence or polarization of molecules at the waveguide surface while minimizing measurement the fluorescence, absorbance, luminescence or polarization of molecules in the surrounding solution which are not at the fiber surface. Such an apparatus is known to one skilled in the art as an evanescent sensing apparatus.

3a: A sensor cartridge which enables the treated surface of the optical waveguide of component (1a) to contact test solutions.

4a: A means of positioning said sensor cartridge in said optical apparatus so as to enable measurement of fluorescence, absorbance or luminescence of molecules at the waveguide surface.

5a: A means of acquiring data from the optical apparatus.

6a: At least one solution containing a plurality of said certain molecule of biological interest, said plurality of molecules having been tagged with molecules belonging to that class of chemicals which interact with light in a manner so as to alter the transmission of light by means such as and without limitation, absorbance, fluorescence, luminescence, or polarization; or which produces a second chemical which interacts with light in said manner, such as and without limitation, an enzyme having action producing or destroying a fluorescent, absorbing, luminescent or polarizing compound. The molecular tag may be chemically attached to said plurality of molecules or it may be chemically attached to a molecule such as and without limitation, an antibody, having affinity for said certain molecule of biological interest. It is important that said certain molecule of biological interest be tagged in a manner which does not prevent the binding of said certain molecule of biological interest to said specific structural features of said optical waveguide.

When used according to the methods set forth in the present invention, said solution is diluted to yield two solutions, the first being such that it produces a small but reliable sensor response and the second being at a concentration at least 2 times that of the first, said second solution being of a concentration such that measurements may be made in the physiological concentration range of interest. Said first solution comprises a calibration standard and said second comprises a zero competition sample. In some embodiments, sample solutions having composition similar to that of said zero competition sample with the addition of a sample specimen, compound or collection of compounds which are to be tested are also created. It is important that the concentration of said calibration standard be low enough so that it not occupy a significant fraction of the available sites on the fiber by the end of the calibration run. Said diluted solutions are created in an assay diluent comprising buffering substances to maintain pH, ions as needed to create an ionic composition so as to optimize the stability and functioning of the biological molecules under study, protease inhibitors, proteins which reduce nonspecific interactions and any other specific components needed to maintain the integrity of the biological molecules under study. If a nucleotide comprises either the specific feature on said waveguide or said biological molecule of interest, a plurality of molecules, such as and without limitation polydeoxyinosine-deoxycytosine, will also be added so as to reduce nonspecific interactions with the nucleotide of interest.

7a: If the sensor apparatus being used produces scattering of light into the solution surrounding said waveguide, then two additional solutions are needed to establish a correction for signal due to such scatter, both being comprised of tagged molecules belonging to a class of chemicals which do not bind to the waveguide surface in assay diluent, said concentrations of tagged molecules in the two solutions being similar to the concentrations of tagged molecules in said calibration standard and zero competition sample.

The methods of the objects of the present invention have in common steps comprising:

1m: Said tagged binding molecules are combined with the sample on which the measurement is to be performed, and allowed to incubate for a time sufficient to achieve significant binding between said binding molecules and said protein in said sample. Whatever time is chosen, it must be held constant for all samples which are to be compared.

2m: The optical waveguide of component 1a is mounted in the sensor cartridge of component 3a and positioned in optical apparatus of component 2a, by means of positioning means of component 4a, such that light at or near the critical angle for the waveguide is focused and injected into the waveguide.

3m: If necessary, a solution containing a chemical which reduces nonspecific binding to the waveguide by the particular biological molecule of interest, is brought into contact with the sensor waveguide surface for a period sufficient to achieve requisite reduction of non-specific binding.

4m: A measurement is taken on this solution using means of component 5a. This measurement comprises the quantity used in later calculations designated as "optical background." If background is very low in comparison to signal, this step may be eliminated.

5m: If the sensor apparatus being used produces scattering of light into the solution surrounding said waveguide, then the solutions of component 7a are brought into contact with the sensor waveguide surface and measurements are recorded by using means of component 5a. These measurements comprise the quantities which will be used in later calculations and designated as "calibration scatter background" and "sample scatter background." If scatter is very low in comparison to signal, this step may be eliminated.

6m: Said calibration standard of component 6a is brought into contact with the sensor waveguide surface and data comprising paired measurements of sensor output and time elapsed since the solution was first brought into contact with the sensor waveguide surface, is acquired using means of component 5a over a period sufficient to describe either or both (a) the initial rate at which said tagged plurality of a certain molecule of biological interest, binds to the waveguide surface and/or (b) the rate at which said tagged plurality of a certain molecule of biological interest, binds to said waveguide surface once a diffusion controlled rate is reached. If the particular composition of said calibration standard is such that bubbles tend to be caught in said sensor cartridge when solutions are changed, then methanol may be injected into said sensor cartridge both before and after said calibration standard is brought into contact with said sensor waveguide surface.

7m: Said calibration standard is removed from the sensor and said zero competition sample or one of said sample solutions of component 6a is brought into contact with the sensor waveguide surface and data comprising paired measurements of sensor output and time elapsed since the solutions was first brought into contact with the sensor waveguide surface, is acquired using means of component 5a using a timing paradigm identical to that used in said step 6m.

8m: If an actual affinity constant is desired for binding between said biological molecule of interest and said specific binding feature of said optical waveguide, following data acquisition from said fiber surrounded by said sample, said sample is removed and said assay diluent containing no tagged molecules, is injected into said sensor cartridge and data is similarly acquired as said tagged biological molecule of interest is released from binding to the fiber. This measurement, provides the off rate for binding, and typically takes significantly longer than the initial measurement, which provides the on rate of binding.

9m: The real time data describing the binding between said biological molecule of interest and said specific binding feature on said optical waveguide is processed in different ways, depending upon the desired outcome. A procedure is provided whereby the activity of a sample relative to a calibration solution is calculated. A second procedure is provided for the calculation of an affinity constant for binding between said certain biological molecule of interest and said specific binding feature of said optical waveguide. A third procedure is provided for calculating the net binding constant when said receptor exhibits co-operative binding.

Procedure for Determining Relative Sample Activity (S/C)

1. If step 5m was necessary, then subtract said calibration scatter background from all data obtained in step 6m. If step 5m was unnecessary, then subtract said optical background from all data obtained in step 6m.
2. If step 5m was necessary, then subtract said sample scatter background from all data obtained in step 7m. If step 5m was unnecessary, then subtract said optical background from all data obtained in step 7m.
3. Divide the results of step 2 by those of step 1 for each point.
4. Graph the outcome of step 3 on the y-axis versus on the x-axis, the amount of time which has elapsed since solutions were brought into contact with the sensor waveguide surface. This will result in a graph which will change rapidly during the period of initial binding, but will settle to a more or less horizontal straight line once the diffusion controlled period of data acquisition is reached.
5. Average the y values over at least 6 of the last data points in the straight line region of the graphs obtained in step 4. The quantity derived in said fashion is hereafter referred to as "S/C." A normal range for S/C is established and used to identify samples which exhibit atypical sample activity. Said sample activity, which is often the quantity of interest in comparing biological samples, represents the product of the concentration of said biological molecule of interest in the sample and the affinity constant of said biological molecule of interest and said specific binding feature of said optical waveguide. If it is reasonable to assume that $K_\alpha$ for the sample and for the calibration standard are identical, then S/C is equal to the concentration of said biological molecule of interest in the sample divided by the concentration of the concentration of said biological molecule of interest in the calibration standard. If said calibration standard is created so as to have a known concentration, then the concentration of the said biological molecule of interest in the sample can be calculated by multiplying the quantity S/C by the concentration of said calibration standard.

Specific Means of the Objects of the Present Invention

According to the first object of the present invention, a method and apparatus are provided which utilizes biological receptors as reagents for identification of compounds having potential for producing disruption of a biological regulatory system, including and without limitation the reproductive system, and other endocrine systems. In a first embodiment of component 1a, the sensor waveguide feature which binds a biological receptor, said features conferring upon said molecules or polymers a binding affinity for a certain molecule of biological interest resembles a specific ligand for a biological receptor, and said certain molecule of biological interest resembles a biological receptor or portion thereof, said biological receptor or portion thereof also comprising said certain molecule of biological interest in component 6a. Also according to the first object of the present invention, in a second embodiment of component 1a, said features conferring upon said molecules or polymers a binding affinity for a certain molecule of biological interest of resembles the specific nucleotide sequence of the response element for said receptor or a portion thereof, and said certain molecule of biological interest resembles a biological receptor or portion thereof, said biological receptor or portion thereof also comprising said certain molecule of biological interest in component 6a. Test samples of component 6a are comprised so as to compare binding between said biological receptor and said binding feature of components 1a in the absence of the compound being tested, and in the presence of at least one concentration of said compound. If said test compound alters the quantity S/C for either type of component 1a, said test compound has potential for producing disruption of a biological regulatory system.

It is a second object of the present invention to provide a method and apparatus for evaluating the presence or absence of estrogen mimics in an aqueous sample. According to the second object of the present invention, in component 1a, said features conferring upon said molecules or polymers a binding affinity for a certain molecule of biological interest of resembles a specific ligand for a the estrogen receptor, and said certain molecule of biological interest resembles an estrogen receptor or portion thereof, said estrogen receptor or portion thereof also comprising said certain molecule of biological interest in component 6a. Also according to the second object of the present invention, in component 1a, said features conferring upon said molecules or polymers a binding affinity for a certain molecule of biological interest of resembles the specific nucleotide sequence of the response element for said estrogen receptor or a portion thereof, and said certain molecule of biological interest resembles the estrogen receptor or portion thereof, said estrogen receptor or portion thereof also comprising said certain molecule of biological interest in component 6a. Test samples of component 6a are comprised so as to compare binding between said estrogen receptor and said binding feature of components 1a in the absence of the compound being tested, and in the presence of at least one concentration of said compound. If said test compound alters the quantity S/C for either type of component 1a, said test compound may act as an estrogen mimic.

It is a third object of the present invention to provide a method and apparatus for evaluating the presence or absence of progesterone mimics in an aqueous sample. According to the third object of the present invention, in component 1a, said features conferring upon said molecules or polymers a binding affinity for a certain molecule of biological interest of resembles a specific ligand for a the progesterone receptor, and said certain molecule of biological interest resembles a progesterone receptor or portion thereof, said progesterone receptor or portion thereof also comprising said certain molecule of biological interest in component 6a. Also according to the third object of the present invention, in component 1a, said features conferring upon said molecules or polymers a binding affinity for a certain molecule of biological interest of resembles the specific nucleotide sequence of the response element for said progesterone receptor or a portion thereof, and said certain molecule of biological interest resembles the progesterone receptor or portion thereof, said progesterone receptor or portion thereof also comprising said certain molecule of biological interest in component 6a. Test samples of component 6a are comprised so as to compare binding between said progesterone receptor and said binding feature of components 1a in the absence of the compound being tested, and in the presence of at least one concentration of said compound. If said test compound alters the quantity S/C for either type of component 1a, said test compound may act as a progesterone mimic.

It is a fourth object of the present invention to provide a method and apparatus for evaluating the presence or absence of testosterone mimics in an aqueous sample. According to the fourth object of the present invention, in component 1a, said features conferring upon said molecules or polymers a binding affinity for a certain molecule of biological interest of resembles a specific ligand for a the testosterone receptor, and said certain molecule of biological interest resembles a testosterone receptor or portion thereof, said testosterone receptor or portion thereof also comprising said certain molecule of biological interest in component 6a. Also according to the fourth object of the present invention, in component 1a, said features conferring upon said molecules or polymers a binding affinity for a certain molecule of biological interest of resembles the specific nucleotide sequence of the response element for said testosterone receptor or a portion thereof, and said certain molecule of biological interest resembles the testosterone receptor or portion thereof, said testosterone receptor or portion thereof also comprising said certain molecule of biological interest in component 6a. Test samples of component 6a are comprised so as to compare binding between said testosterone receptor and said binding feature of components 1a in the absence of the compound being tested, and in the presence of at least one concentration of said compound. If said test compound alters the quantity S/C for either type of component 1a, said test compound may act as a testosterone mimic.

It is a fifth object of the present invention to provide a method and apparatus for measuring the binding of certain compounds to biological receptor molecules which overcomes the various disadvantages of the prior art.

Procedure for Determining an Affinity Constant

According to the fifth object of the present invention, a procedure for processing data obtained using the described apparatus and method to yield an affinity constant for binding between said biological receptor and said specific binding feature of said optical waveguide, said affinity constant being calculated from the equations:

$$K_a = k_{on}/k_{off} \qquad \text{Equation 2}$$

$$\text{signal at time (t)} = k_{on}\epsilon\log[P][N] \qquad \text{Equation 3}$$

where $k_{on}$ and $k_{off}$ are both derived from real time data obtained, $\epsilon$=a constant which relates the signal read by the sensor to the moles of tagged molecules bound to the surface of the sensor fiber.

[P]=the concentration of said certain molecules of biological interest,

[N]=the concentration of said binding molecules on said sensor fiber.

Equations of a similar type pertaining to second or third order kinetics, as may be found in any text on physical biochemistry, may be substituted as is appropriate.

Once data has been automatically acquired, affinity constants may be calculated from equations 2 and 3 using known concentrations of said certain molecule of biological interest in place of [P] in equation 3. The value of the factor $\epsilon$, which converts the sensor reading to a molar concentration of said tagged certain molecules of biological interest can be determined by performing the steps which give the S/C value for a single solution containing no competing ligand. Said solution is then removed and used a second time in a second sensor in exactly the same manner. The concentration of said tagged certain molecules of biological interest calculated from the S/C value obtained with the second sensor is then subtracted from the concentration of said tagged certain molecules of biological interest calculated from the S/C value obtained with the first sensor. The moles of said tagged certain molecules of biological interest which would have to be removed from the solution to result in this concentration change for the volume of liquid contained in the sensor correspond to the moles of said tagged certain molecules of biological interest on the first sensor fiber. Division of the final reading from the first fiber sensor by the moles of said tagged certain molecules of biological interest on the first sensor fiber provides the factor, $\epsilon$.

The $K_d$ for binding between unliganded said certain specific molecules of biological interest, such as and without limitation a biological receptor protein and the subsequent molecular component of a signal transduction pathway such as and without limitation, a DNA molecule, is calculated using equation 4. The derivation is carried out in terms where said certain specific molecules of biological interest comprises a biological receptor, R.

$$K_d = k_{off}/k_{on} = [L_S][R]/[RL_S] \qquad \text{Equation 4}$$

where $K_d$=The dissociation constant between the sensor and the waveguide.

$k_{off}$=The initial slope of the line obtained by plotting the sensor output obtained in step 8m when the solution of component 6a contains none of the test compound (the zero point for the series of test solutions) versus time. Said slope is then multiplied by a factor describing the number of moles of tagged receptor bound to the sensor per unit of sensor output.

$k_{on}$=The initial slope of the line obtained by plotting the sensor output obtained in step 8m when the solution of component 6a contains none of the test compound (the zero point for the series of test solutions) versus time and multiplying said slope by a factor describing the number of moles of Lagged receptor bound to the sensor per unit of sensor output.

$L_s$=The concentration on the waveguide surface of the molecular feature which acts as a binding ligand for the receptor.

R=The concentration of unbound receptor in the solution.

$RL_s$=The concentration of receptor bound to the waveguide surface. This is the measured signal generated by the sensor multiplied by a factor describing the number of moles of tagged receptor bound to the sensor per unit of sensor output.

The relationship between the concentration of receptor added to the solution that which is bound is expressed by Equation 5.

$$[R_{total}] = [R] + [RL_s] \qquad \text{Equation 5}$$

Combining Equations 4 and 5 provides a form from which a meaningful data plot can be derived.

$$K_d = k_{off}/k_{on} = [L_s][R_{total} - [RL_s]]/[RL_s] \qquad \text{Equation 6}$$

The value of $k_{on}$ is calculated using the starting value of:

$R_{total}$=the concentration of receptor initially placed in the solution, and $[RL_s]=0$.

The value of $k_{off}$ is calculated using the starting value of:

$R_{total}$=0 concentration of receptor initially placed in the solution, and $RL_s$=(sensor reading just when buffer was added)×(factor to convert sensor reading to molar concentration of $[RL_s]$).

$[L_s]$ is determined by allowing a fiber to incubate with an excess of tagged receptor until the signal from the sensor no longer rises. That value is then multiplied by the factor which converts sensor reading to molar concentration of $[RL_s]$.

A Method for Determining Bindint Constants for Receptors Exhibiting Co-operatve Binding Also according to the fifth object of the present invention, biological molecules displaying cooperative binding of ligands may be investigated by a unique method of the present invention. This method overcomes the disadvantages of the prior art in that it does not require radioactive labels and it does not require that an equilibrium condition be reached prior to measurement. A fiber optic sensor which is configured for operation in competitive assay offers a convenient method for study of cooperativity in binding. Binding of one molecule of ligand to a macromolecules displaying cooperativity increases the affinity constant of the macromolecule for binding of the second ligand. In the case of a fiber optic sensor in which ligand is on the fiber, this gives rise to an unusual profile for a competition curve. Under conditions of non-cooperativity, the initial uncompeted reading from the fiber sensor is the highest reading. Each increasing amount of competitor brings a decreasing fiber sensor response. However, if cooperativity is present, the competition curve rises in response to very low concentrations of competitor, reaching a peak response at some concentration and then dropping as the concentration of competitor continues to increase. The mathematics and forms relating in general to cooperative binding are thoroughly described in the book *Physical Biochemistry. Applications to Biochemistry and Molecular Biology* by David Freifelder; W. H. Freeman and Co., New York; 1982, p 655–684. This text is fully and completely incorporated herein by reference, word for word and paragraph for paragraph.

According to the method of the present invention, the specific binding feature of component 1a is a plurality of molecules which act as a ligand for said certain molecules of biological receptor. Calibration solutions of component 6a comprise a low concentration of tagged said certain molecules of biological receptor, said calibration solutions being essentially identical for all samples. Several standard sample solutions of component 6a are created, each comprising a fixed higher concentration of tagged said certain biological molecules to which has been added one of a series of specific concentrations of a ligand of known binding affinity (Ligand A). Additionally, a series of several test sample solutions are created, the concentrations of ligand (Ligand B) in said test samples being identical to those of Ligand A in said series of standard samples. All solutions are tested using identical protocols according to the method comprising steps 1m–7m of the present invention. It is important that the experiment be conducted in a manner such that the time between addition of the sample ligand to the solution containing the molecules of biological receptor be the same for all test solutions of both Ligand A and Ligand B.

For solutions containing a test compound which binds to said certain specific biological receptor in a way which induces cooperativity, certain low concentrations of the test compound will produce a quantity S/C from step 9m which is higher than the theoretical ratio. As the concentration of test compound is increased, the quantity S/C will drop from the increased value seen at low concentrations, finally falling below the theoretical ratio and continuing to drop until saturation is reached. If the test compound binds to said certain molecules of biological receptor in a way which does not induce cooperativity, the quantity S/C will drop below the theoretical ratio even at low concentrations and continue the drop as the concentration of test compound increases until saturation is reached.

This method provides a simple direct means for quickly determining (1) whether the test compound binds to said molecules of biological receptor, and (2) whether the test compound binds in a manner so as to induce cooperative binding between said certain molecules of biological receptor and additional ligands. Since receptor binding is the first step in affecting biological regulatory mechanisms, this simple procedure provides a method for rapidly screening samples to detect the presence of compounds having potential to disrupt certain biological control mechanisms involving the biological receptor used in testing. This type of screening is particularly well suited to testing environmental samples.

In order to enable calculation of the effective binding constant ($K_R$) between a certain test compound and said certain specific biological receptor, a method is presented for calculating that constant relative to that of a compound having a known effective binding constant for said certain specific biological receptor. Said effective dissociation constants represent the net effect of two different dissociation constants in molecules exhibiting cooperative binding.

$$\frac{K'_R}{K_R}[L_s] = L \qquad \text{Equation 7}$$

where $K'_R$=the known binding constant between a specific ligand and said certain specific biological molecules of interest $K_R$=the unknown binding constant between a certain test compound and said certain specific biological molecules of interest, the known binding constant between a specific ligand and said certain specific biological molecules of interest, $[L_S]$=the concentration of the test compound at which the peak signal occurs, and $[L]$=he concentration of the known ligand at which the peak signal occurs.

By first running a fiber sensor with said standard sample solutions containing ligand having a known $K'_R$ for said certain specific biological molecules of interest, the quantity $K'_R$ can be calculated from the concentration at which the peak reading occurs. This $K'_R$ can then be used with data from said test sample solutions containing a series of concentrations of ligand of unknown $K_R$ to determine the $K_R$ of that ligand for the receptor.

Thus the $K'_R$ for the test compound can be calculated from sensor data and knowledge of the $K'_R$ for the known ligand.

The mathematical basis for data treatment utilizing equation 3 is herein described in terms where said biological molecule is a receptor having concentration [R]. If the competitor is incubated with the receptor prior to injection into the fiber sensor, the situation prior to injection is described in terms of variables typically employed in a Hill plot for determining cooperativity by the equations:

$$\frac{v}{n-v} = K_T[L] \quad \text{as } [L] \text{ approaches } 0, \text{ and}$$

$$\frac{v}{n-v} = K_R[L] \quad \text{as } [L] \text{ approaches } \infty$$

Where

V=Total number of occupied ligand sites.

n=Total number of ligand site.

$K_T$=Microscopic binding constant for unliganded receptor.

$K_R$=Microscopic binding constant for monoliganded receptor.

[L]=Concentration of competitor in solution.

Upon injection, the binding of the ligand on the fiber to the receptor is described by the equations given below. If $K_R > K_T$, then as [L] increases, $[RL_S]$ increases until the biliganded dominates the following equations:

$$[RL_s] = L_s](K'_T[R_0] + K'_R[R_1])$$

$$[R_T] = [R_0] + [R_1] + [R_2]$$

$$[R_1] = K_T[R_0][L]$$

$$[R_2] = K_R[R_1][L] = K_T K_R[R_0][L]^2$$

Where $[RL_s]$=receptor bound to fiber.

[L]=concentration of ligand in the solution.

$[L_s]$=concentration of ligand on the fiber.

$[R_T]$=Total concentration of receptor.

$[R_0]$=concentration of unliganded receptor in solution after incubation with competitor.

$[R_1]$=concentration of monoliganded receptor in solution after incubation with competitor.

$[R_2]$=concentration of biliganded receptor in solution after incubation with competitor.

$K'_T$=microscopic binding constant between fiber ligand and unliganded receptor.

$K'_R$=microscopic binding constant between fiber ligand and monoliganded receptor.

The measurable signal from the fiber optic sensor is proportional to $[RL_s]$. For positive cooperativity, $k_R > k_T$. Consequently, by the time the peak signal is reached, $[R_1]$ is sufficiently greater than $[R_0]$ so that the latter can be ignored. As [L] is increased, the condition at which the peak signal occurs is described by:

$$K'_R[L_s][R_1] = [R_2] = K_R[L][R_1]$$

This can be rearranged to predict the concentration at which the peak will occur.

$$\frac{K'_R}{K_R}[L_s] = [L] \qquad \text{Equation 8}$$

Although the foregoing equations are descriptions of equilibrium conditions, their validity for application to nonequilibrium data obtained from fiber optic sensors derives from the observation that for first order kinetics, t, the time interval required for obtaining any given extent of binding, x, is given by the equation:

$$\tau = \frac{1}{k}\ln\frac{1}{1-x}$$

where k is the kinetic constant for the binding.

Thus as long as the time the test ligand and the biomolecule are in contact, and the precise moment of introduction of sample mixture into the fiber sensor remain constant, the above mathematical derivation applies because comparisons are always carried out at a time corresponding to the same fractional extent of equilibrium binding.

According to the sixth object of the present invention, the methods of the fifth object of the present invention are applied to investigation of binding between biological receptor molecules which play a crucial role in transduction of a signal initiated by the binding of a ligand to a biological macromolecule such as and without limitation, binding of a receptor to its nuclear response element in response to binding of the receptor to a steroid. Specifically, in component 1a, said features conferring upon said molecules or polymers a binding affinity for a certain molecule of biological interest resembles the binding region of the response element for said receptor or a portion thereof, and said certain molecule of biological interest resembles said receptor or portion thereof, said receptor or portion thereof also comprising said certain molecule of biological interest in component 6a.

According to the seventh object of the present invention, a method is provided for measuring the impact of certain compounds on the binding of biological receptor molecules to other molecular components comprising a biological signal transduction mechanism. The method described in the fifth object of the invention is carried out using a sensor cartridge of component 1a in which said features conferring upon said molecules or polymers a binding affinity for a certain molecule of biological interest, resembles the molecule in said signal transduction mechanism to which said biological receptor binds. Calibration standard of component 6a solutions comprise a low level of said tagged biological receptor. Test sample solutions of component 6a comprise a concentration of said tagged biological receptor, said concentration being held constant and being set to approximate a relevant in vivo concentration of said biological receptor, and also comprising a concentration of the compound to be tested. are used in the manner of the fifth object of the invention. Several test samples having different concentrations of a given test compound are compared with a similar test sample having no test compound present using procedures described in the fifth object of the present invention. The impact which the test compound at a given concentration, has upon binding between said biological protein and said molecule in said signal transduction mechanism to which said biological receptor binds, may be assessed by comparing the value of S/C for the sample without test compound with that of the sample containing a given concentration of the test compound.

According to the eighth and ninth objects of the present invention, real time data acquisition is provided when said evanescent sensing apparatus created by components 1a–7a utilizes as component 5a an automated means of computer controlled data acquisition employing a timing paradigm which is rapid enough to capture the measurable changes in signal. Typically this is on the order of 2–4 seconds between data points.

According to the tenth object of the present invention, a method is provided for evaluation of potential for certain compounds to act as chemotherapeutic agents for treatment of hormone dependent cancers. Component 1a is comprised so that said features conferring upon said molecules or polymers a binding affinity for a certain molecule of biological interest resembles the specific nucleotide sequence of the response element for that biological receptor which serves as the primary recognition molecules for the hormone of said hormone-dependent cancer or a portion thereof. Calibration standard of component 6a comprises a concentration of that biological receptor which serves as the primary recognition molecules for the hormone of said hormone-dependent cancer or a portion thereof, said receptor having been tagged as described according to the manner of component 6a. Test samples of component 6a are prepared from frozen tissue biopsy in a manner known to those skilled in the art to produce a cytosol extract of said tissue biopsy. Said cytosol extract is tagged according to the methods of component 6a. Test samples of component 6a are comprised so as to compare binding between said biological receptor in said cytosol extract and said binding feature of components 1a in the absence of the compound being tested, and in the presence of at least one concentration of said compound. If said test compound significantly reduces the quantity S/C, said test compound has potential as a possible chemotherapeutic agent for treatment of said hormone dependent cancer.

According to the eleventh object of the present invention, a method and apparatus is provided for assessing the type of impact (such as inhibitory impact or excitatory impact) on biological regulatory systems a certain compound will be likely to exert. The method described in the fifth object of the invention is carried out using two types of a sensor cartridges of component 1a. In the first, said features conferring upon said molecules or polymers a binding affinity for a certain molecule of biological interest, resembles the molecule in said signal transduction mechanism to which said biological receptor binds. In the second, said features conferring upon said molecules or polymers a binding affinity for a certain molecule of biological interest, resembles a known ligand for said biological receptor. Calibration standard of component 6a solutions comprise a low level of said tagged biological receptor. Test sample solutions of component 6a comprise a concentration of said tagged biological receptor, said concentration being held constant and being set to approximate a relevant in vivo concentration of said biological receptor, and also comprising a concentration of the compound to be tested. are used in the manner of the fifth object of the invention. Several test samples having different concentrations of a given test compound are compared with a similar test sample having no test compound present using procedures described in the fifth object of the present invention. The impact which the test compound at a given concentration, has upon binding between said biological protein and said molecule in said signal transduction mechanism to which said biological receptor binds, may be assessed by comparing the value of S/C for the sample without test compound with that of the sample containing a given concentration of the test compound. With reference to sensors waveguides having attached nucleotide sequence of said nuclear response element, if S/C for test samples is equal to or lower than S/C for a sample containing no test compound, and if with reference to sensor waveguides having attached ligand, S/C is also lower, then the test compound is inhibitory. With reference to sensor fibers having attached nucleotide sequence of said nuclear response element, if S/C for test samples is higher than that of a sample containing no test compound, then the test compound is excitatory. If S/C remains constant for both waveguide types, then the test compound is neither excitatory nor inhibitory.

According to the twelfth object of the present invention a method and apparatus are provided for assaying the amount of a particular receptor, such as and without limitation estrogen receptor, progesterone receptor and testosterone receptor present in tissue biopsy, which goes beyond prior art in providing a rapid and simple means of identifying both active and inactive receptor. The method described in the fifth object of the invention is carried out using two types of a sensor cartridges of component 1a. In the first, said features conferring upon said molecules or polymers a binding affinity for a certain molecule of biological interest, comprises a specific nucleotide sequence or portion thereof which resembles the response element for said biological receptor. In the second, said features conferring upon said molecules or polymers a binding affinity for a certain molecule of biological interest, comprises an antibody for said biological receptor. Calibration standards of component 6a comprise solutions comprise a low level of said tagged biological receptor. Sample solutions of component 6a comprise cytosol extracts from tissue biopsy samples, said extracts having been incubated for a certain time with a tagged antibody to said biological receptor, said tagged antibody being directed toward a site on said biological receptor such that said receptor maintains its native binding affinity toward the binding features of both types of components 1a. Said cytosolic extract is prepared in a solution of a type described as assay diluent in the description of component 6a. A certain portion of said cytosolic extract is used with a sensor having component 1a possessing specific binding feature comprising said antibody for said biological receptor. To a certain second portion of said cytosolic extract is added a certain concentration of a ligand having known affinity for said particular receptor. Said second portion is then used with a sensor having component 1a possessing specific binding feature comprising said specific nucleotide sequence or portion thereof which resembles the response element for said biological receptor. A control sample comprising a physiological concentration of tagged receptor from a standardized receptor preparation, is assayed using sensors of both types of component 1a in a manner identical to that used with the biological receptor. The S/C value for that portion run on said antibody possessing sensor, multiplied by the concentration of tagged receptor in said calibration standard represents the concentration of biological receptor in the biopsy sample. The S/C value for that portion which is run on said nucleotide possessing sensor reflects the activity of said biological receptor. Molar activity for the cytosolic extract is compared with that of the standard sample.

SPECIFIC EXAMPLES OF THE PREFERRED EMBODIMENTS OF THE PRESENT INVENTION

First Example of the Preferred Embodiment

The first example of a preferred embodiment of the present invention is a fiber optic sensor having components and method adapted to identify the presence of estrogen mimics in a liquid sample; and to perform measurements from which may be calculated the effective $K_d$ of the estrogen mimic in the sample for recombinant human estrogen receptor; and to assess the effect of said estrogen mimic on biological response through estrogenic signal transduction mechanisms. To these ends, components of an evanescent fiber optic sensor were constructed as described below. Component 1a, a chemically sensitized optical waveguide, takes two forms, type 1 which provides a surface possessing features which resembles the estrogenic compound estrone-3-glucuronide, and type 2 which provides a surface which resembles the nuclear response element which binds human estrogen receptor in vivo. Type 1 fibers are used to obtain information leading to calculation of the effective $K_d$ of the estrogen mimic in the sample for recombinant human estrogen receptor. Type 2 fibers provide quantification of the binding of the estrogen receptor to its nuclear response element in the presence and absence of sample being tested. They are used to assess the impact of the sample on the biological response through estrogenic signal transduction mechanisms.

To further understand the present invention as it relates to the first preferred embodiment, details first of the components and then of method of utilization follow.

Component 1a Type 1
  Preparing Optical Fibers Having Estrone-3-Glucuronide Surface Features 400 μm step indexed, multi-mode, fused silica fiber clad with amorphous copolymers of perfluoro (2,2-dimethyl-1,3 dioxide) and tetrafluoroethylene (e.g.Teflon AF™), Product #FSU400 420, was obtained from Polymicro Technologies Inc., 18019 N. 25th Ave., Phoenix, Ariz., 85023-1200. Fiber was cleaved using a York Electronic Fiber Cleaver to yield 10 cm pieces with optically acceptable end faces. Pieces were cleaned by sonication in methanol for 30 minutes and the end cladding was protected by covering one end with a 1 cm and the other end with a 1.5 cm piece of #25 black polyimide tubing, 0.002 wall, (from HV Technologies, Inc., P.O. Box 948, Trenton, Ga. 30752) and heat shrinking the tubing so that it seals itself around the cladding. This protects the cladding from being dissolved away by subsequent chemical procedures. The refractive index of this cladding prevents light from leaking out of the fiber where the fiber contacts the sensor cartridge ends. It is therefore important that the cladding be protected on the parts of the fiber which will contact other sensor components. A quantity of fibers (up to 64 at a time) was then placed in a carrier which holds the fibers vertically in a reservoir so that fibers were surrounded by chemicals which were injected and removed using a syringe. The reservoir was filled with a fluid capable of slowly dissolving off the cladding of the fibers so that the amount of cladding which remains behind could be regulated by controlling the time a batch of fibers was exposed to said fluid. In the present embodiment, said fluid was FLUORINERT a fluid capable of dissolving off the cladding of fibers FC-75™ obtained from the Specialty Polymers Division of the DuPont Company. Fibers were exposed to Fluorinert FC-75™ a fluid capable of dissolving off the cladding of fibers for about thirty to about forty-five minutes. The fibers were then rinsed twice with additional Fluorinert FC-75™ and once with methanol and fibers and reservoir were placed in the entry chamber of a dry box and dried under vacuum for 30 minutes. This procedure produced fibers having a surface which was clean except for small islands of amorphous copolymers of perfluoro (22, dimethyl-1,3 dioxide) and tetrafluoroethylene) which remain. The islands prevent large protein molecules from reaching the surface of the fiber, while permitting small molecules used in subsequent chemical sensitization of fibers to reach and react with the bare fiber surface.

Unless otherwise indicated, all reagents used in the reactions which result in sensitized fibers were obtained from Sigma Chemical Co. P.O. Box 14508, St. Louis, Mo. 63178. The fibers and reservoir were transferred into the dry box and the longitudinal surfaces of the fibers were surrounded by a 2% solution of 3-(mercaptopropyl)-trimethoxysilane in anhydrous toluene (Sigma Chemical Co.) for 2 hr at room temperature, creating a glass surface bearing thiol groups. After rinsing in toluene, the thiol groups on the fibers were reacted with the maleimido moiety of the heterobifunctional agent, y-maleimidobutyric acid-Nhydroxysuccinamide ester, hereafter referred to as GMBS (Sigma Chemical Co.) by incubating them in a 2 mM solution of GMBS in anhydrous denatured ethanol (Sigma Chemical Co.) for 1 hour. At this point the methods for the two different types of fibers diverges. For the estrone-3-glucuronide fibers, the succinimide ester of the GMBS is reacted with a 1 mg/ml solution of hexane diamine for 4 hr at room temperature in 0.1 M carbonate buffer, pH 9.3. Following this, 15 mg of estrone-3-glucuronide (Sigma Chemical Co.) and 450 mg of 1-ethyl-3-(3-dimethylaminopropyl)-carbodiimide) were dissolved in water, pH 4.3–4.6 and the fibers were incubated with this solution overnight at room temperature.

Component 1a Type 2

Preparing Fibers Having an ERE Surface Feature

The nucleotide sequence of the estrogen response element from Xenopus Vitellogenen A2 Gene in known to bind the human estrogen receptor protein. Discussion of this may be found in a journal article by Wittliff, J. L., Wenz, L. L., Dong, J., et al., *Expression and Characterization of an Active Human Estrogen Receptor as a Ubiquitin Fusion Protein from Escherichia coli*, J. Biol. Chem. 265(35), 22016–22022 (1990). This text is fully and completely incorporated herein by reference, word for word and paragraph for paragraph. That nucleotide sequence will hereafter be referred to as "the ERE." It is shown below:

'5 GTCCAAAGTCAGGTCACAGTGACCTGAT-CAAAGTT3'

'3 CAGGTTTCAGTCCAGTGTCACTGGAC-TAGTTTCAA5'

A nucleotide of this description, which also incorporated an amine on the G residue of the 5' end of one strand was synthesized by Research Genetics, Inc., 2130 Memorial Parkway SW, Huntsville, AL. 35801. The stands were annealed as follows: 100 μg each of the upper and lower oligonucleotides were combined in 500 μl of a buffer containing 50 mM Tris buffer pH 7.5, 50 mM KC1 and 10 mM $MgCl_2$ and gently vortexed. The tube was floated in 500 ml of hot water (80° C.–90° C.) and allowed to slowly cool for two hours. To this was added 55 μl of 3.0 M NaOAc. The mixture was vortexed and split between two tubes. To each tube was added 830 μl of cold 100% EtOH. The mixture was vortexed, incubated at −20° C. for two hours and centrifuged for 15 minutes in a microcentrifuge in a cold box. The supernatant was removed and the DNA dissolved in 50 ml. Carbonate buffer, for coupling to fibers.

For creating optical fibers having ERE covalently linked to the surface the fibers were prepared, cleaned and silanized with 3-(mercaptopropyl)-trimethoxysilane in dry toluene followed by GMBS as previously described. Following this, 200 μg of the ERE was dissolved in carbonate buffer, pH 9.3 was injected into the fiber processor and incubated for 4 hours at room temperature. Following this, fibers were washed and stored as previously described.

Fibers were rinsed with distilled water, dried with nitrogen and mounted in flow through sensor cartridges of the type shown in FIG. 1. To prevent fluorophore from leaking onto the distal or proximal fiber faces and generating spurious fluorescence, the holes were fibers emerge from the cartridge ends were sealed using 5 minute epoxy. Cells were stored at room temperature until used.

Component 2a

The Optical Apparatus for use with an Evanescent Wave Sensor Cartridge.

The optical apparatus utilized in the preferred embodiments comprises that apparatus which has been described with reference to FIGS. 1–3. Referring to FIG. 1, the optical apparatus utilized to perform the kinetic, binding affinity and binding activity measurements of the present invention is shown. Light from a laser diode (21) having emission wavelength around 635 nm is directed to a dispersive element (20), situated such that light propagating from said light source impinges upon said dispersive element In the preferred embodiment of this invention, said dispersive element comprises a diffraction grating in near Littrow configuration. Said impingent light, upon exiting from said dispersive element, thereafter propagates such that each constituent wavelength component of light is angularly dispersed as a function of wavelength. Said dispersive element functions to angularly separate unwanted wavelength band(s) from wanted wavelength band(s), and to direct all wavelengths to means (22), specifically a turning mirror for directing said angularly dispersed light along a path of substantial distance. Said distance is substantial when the path length is sufficient to spatially separate unwanted wavelength band(s) (25) from wanted wavelength band(s) (24). Blocking element(s) (23) containing apertures, situated at said substantial distance to said dispersive element (20) intercept only unwanted wavelength band(s) (25). Selected wavelength band(s) (24) are not intercepted by said blocking element(s) (23), and thus, continue to propagate.

Said selected wavelength band(s) (24) of light are directed by means (28), such as and without limitation, a beam splitter, a prism or a partially reflective mirror, to pass off axis through focusing means (29) so as to enter the input face of annularizing optical fiber (17) as a narrow beam both off axis and at a specific injection angle to the optical axis so that the beam will first propagate as real skew modes in a substantially confined manner within the annularizing optical fiber (17), said skew modes uniformly distributing the light into a narrow annular band propagating at said specified angle within the annularizing optical fiber (17) and subsequently leaving the first annularizing fiber section and entering into a second fiber section (7) contained within the sensor cartridge (9), said fiber section having been sensitized to substantially react with test and reagent solution(s) only in the presence of a specific chemical. Said focusing means possesses a numerical aperture high enough to match that of annularizing fiber (17), said focusing means comprising a high numerical aperture doublet, said doublet comprising a focusing meniscus lens and piano-convex collimating lens. Annularizing fiber (17) provides means by which excitation light may be shaped to present light to the fiber sensor in the form of an annular ring at or near the critical angle of the sensor. While in one embodiment, a fiber sensor system using the previously described illumination system and incorporating an extended length of fiber preceding the sensitized fiber region could be used to produce a similar shaping of the light beam before it enters the sensitized region of the fiber, the preferred embodiment of the present invention utilizes a separate annularizing fiber (17) to provide a mechanism by which the shaping of the beam remains constant without requiring any adjustments of position as fiber cartridges are replaced. Fiber assembly (7) of sensor cartridge (9) is butt coupled to annularizing fiber (17) by means of coupling capillary (15). In the preferred embodiment, annularizing fiber (17) is a 400 μm fused silica multimode fiber clad with Amorphous copolymers of amorphous copolymers of perfluoro (2,2-dimethyl-1,3 dioxole) and tetrafluoroethylene (e.g.Teflon AF™).

Excitation light passes through sensor cartridge (10) at angles at or near the critical angle, creating an evanescent field which excites fluorescent molecules which are bound to the surface of the sensor fiber. Fluorescence of unbound material is only very minimally excited by this evanescent field. Fluorescence from the molecules bound to said sensor fiber surface is evanescently emitted back into confined propagating modes of said sensor fiber, traveling back through coupling capillary (15), annularizing fiber (17), and focusing means (29). Light of wavelength at or near the excitation wavelength is blocked by band stop filter (26), while light of wavelengths corresponding to fluorescence of molecules bound to the surface of said sensor fiber passes through band stop filter (26) and is focused by means (30) into optical detector (27).

Figure 2:
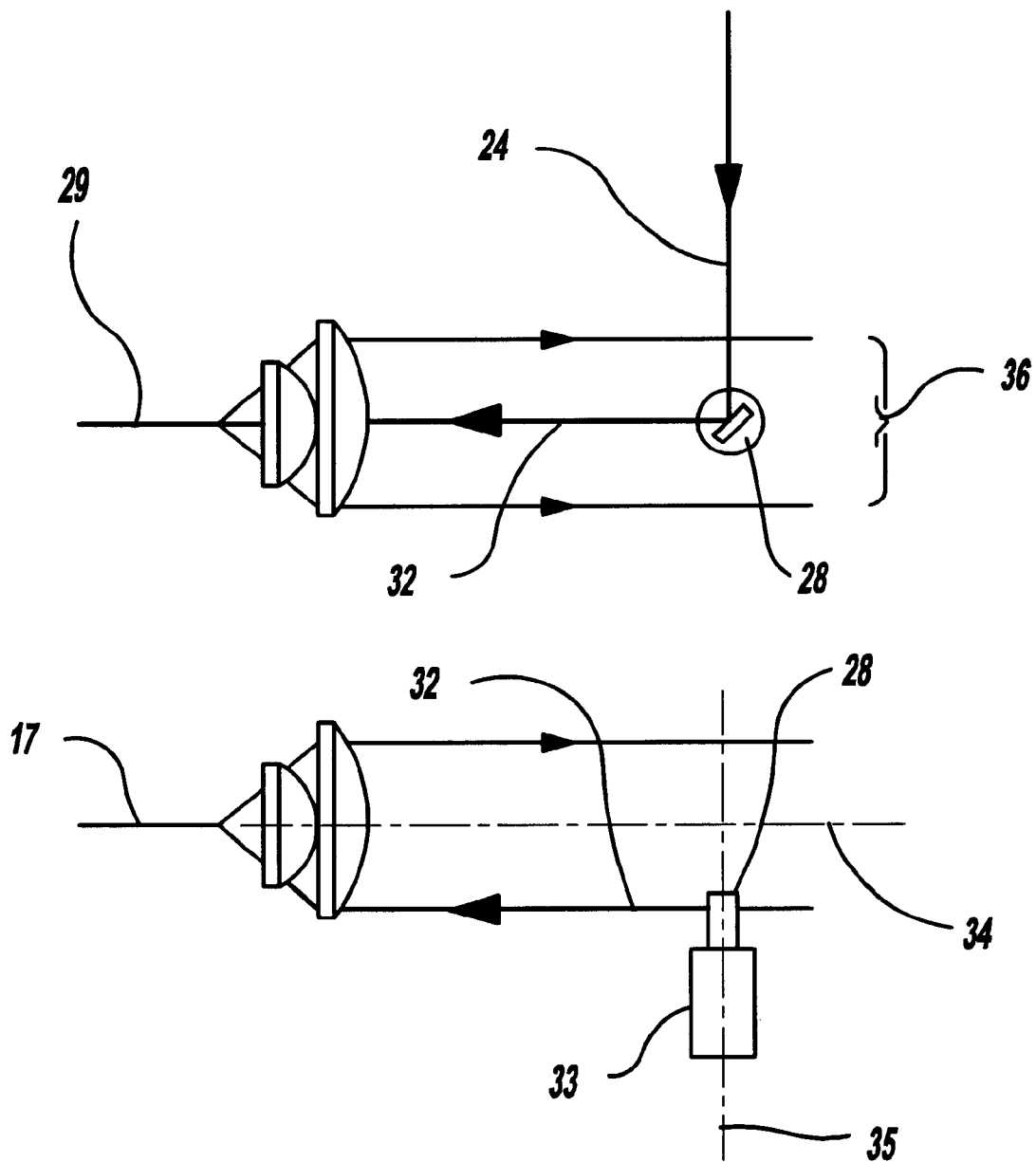
FIG. 2: Shows top and side views of the means of the invention for achieving an annularized excitation beam at or near the proper NA for the fiber in the medium of the sample.

FIG. 2 provides an aid to understanding the manner by which the annular excitation beam of the desired angular distribution is created. An optical axis (34) is established by the position of an injection lens system (29) and an optical fiber (17) with its proximal end near the focal spot of said lens system. A light beam (24) is propagated to intersect the projected aperture (36) of said system on the side opposite from said optical fiber. In the preferred embodiment, said light beam propagates at an angle substantially perpendicular and skew to said optical axis. A redirecting axis is established (35), which is substantially perpendicular to the optical axis, about which a redirecting element (28) may rotate. The preferred embodiment has said redirecting axis intersect with said optical axis. Said redirecting element is positioned to intercept and redirect said light beam at an angle substantially parallel to said optical axis. Said redirecting element may be translated along said redirecting axis so that it protrudes into said projected aperture by an amount just sufficient to intercept said light beam, with all its mounting and manipulating apparatus (33) exterior to said projected aperture. Said light beam may be translated perpendicular to said redirecting axis by an external means, while maintaining interception by concomitant translation of the redirecting element, to affect a change in the perpendicular distance of said redirected beam (32) relative to said optical axis, thereby affecting the injection angle into said optical fiber. Embodiments of the redirecting element may be a mirror, a prism, holographic optical element (HOE), or any other means whereby the beam is redirected to the appropriate angle of parallelism to said optical axis from the transverse angle of said light beam.

Figure 3:
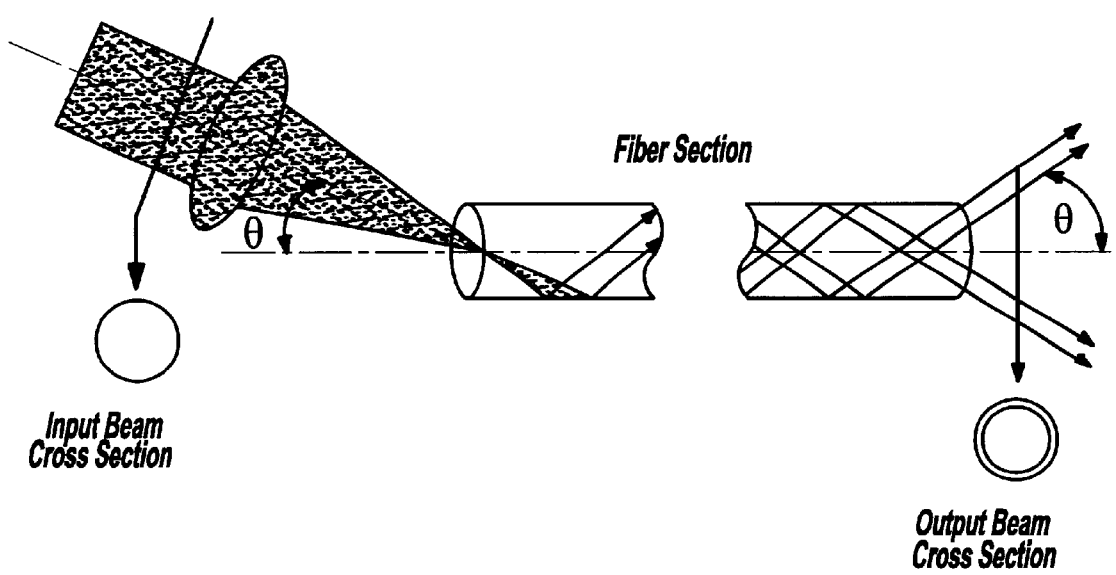
FIG. 3: Presents an idealized picture of annularization of a light beam within an optical fiber.

FIG. 3 presents an idealized picture of what happens to the ray bundle upon entering fiber (17) at angle θ. Said parallel rays of light of said bundle have been focused by an optical element with focal length f into a section of optical fiber of diameter d. When this is done, the beam is forced to propagate through the fiber in high order off axis skew rays and is thus converted to an narrow annular cone with a half cone angle of θ at the output end of the fiber. In any plane perpendicular to the expanding cone, light radiation is concentrated in an annular ring whose thickness is determined by the initial spread in input angles induced by the focusing lens (i.e. determined by its numerical aperture (NA), f/#, or cone angle of the illumination lens) and by the area of inside of the fiber illuminated by the focused beam passing through the front face of the section of optical fiber. For example, as the injected beam diameter and the NA of the illumination objective are made smaller (e.g. NA<0.05), in the absence of other dispersive processes, the annular thickness or the emergent cone will become increasingly narrow and as a consequence, the angular distribution of rays which will be injected into and propagate within the sensor becomes narrowly peaked at the desired critical angle. On the other hand, as the NA of the illumination objective becomes larger (e.g. NA=0.3) or the diameter of the injected beam larger, the annulus will become thicker and because fewer of the ray angles emerging from the annularizer are close to the desired critical angle, the sensitivity of the evanescent fiber sensor will be reduced.

Component 3a
Assembly of the Sensor Cartridge.

Figure 4:
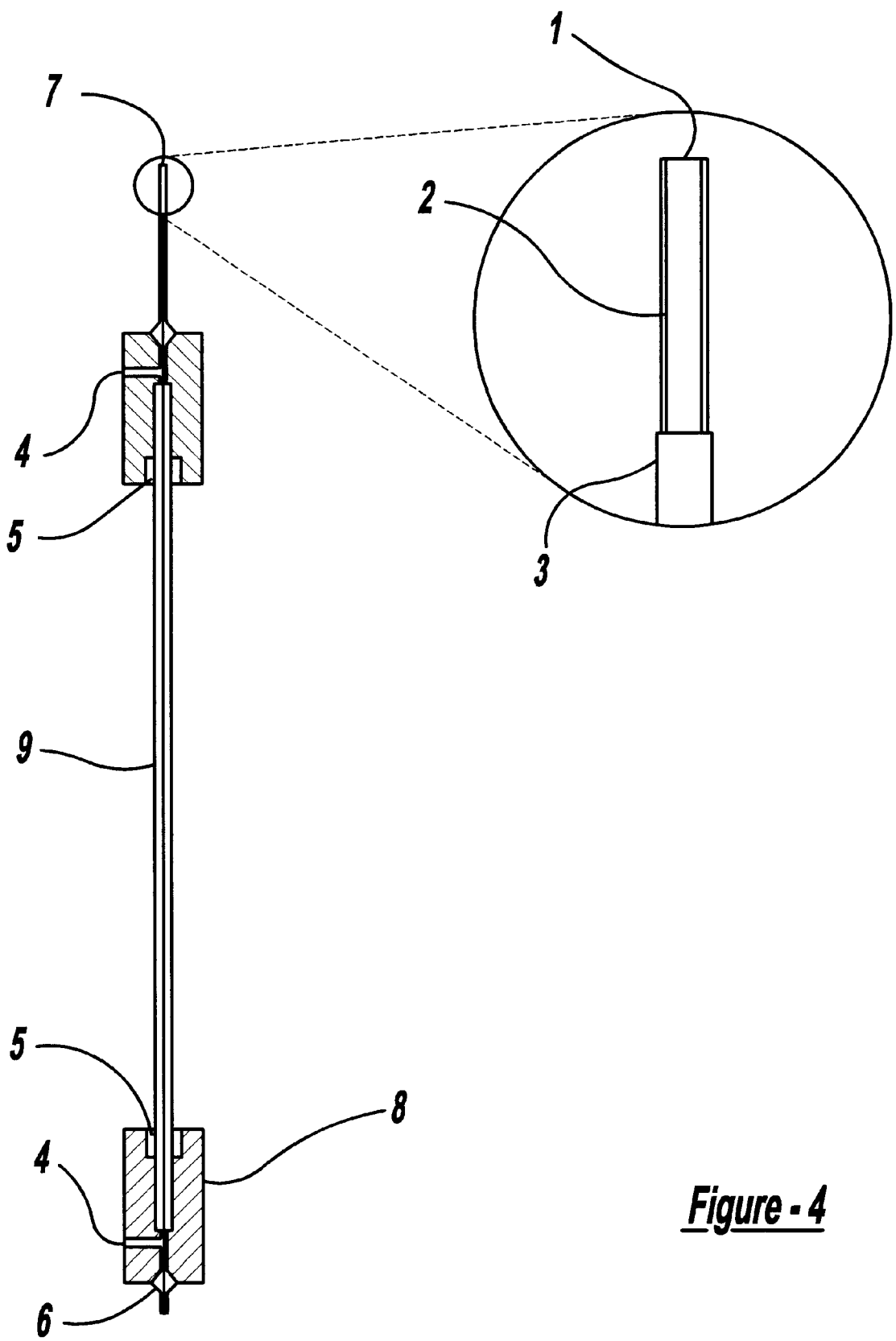
FIG. 4: Shows the sensor cartridge of this invention.

Sensitized fibers of component 1a were rinsed with distilled water, dried with nitrogen and mounted in flow through sensor cartridges of the type shown in FIG. 4, which shows sensor cartridge (10) said cartridge being designed to receive said annular excitation beam and to propagate said beam with high efficiency so as to create an evanescent field along its length, said evanescent field exciting fluorescence in molecules which are bound to the surface of fiber assembly (7), and to receive said fluorescence which is evanescently emitted back into fiber assembly (7), and to propagate said fluorescence back to annularizing fiber (17).

Fluid ferrules (8) position fiber assembly (7) within a cylindrical tube of capillary dimensions (9) which allows fiber assembly (7) to be surrounded by the sample under test. The cylindrical tube (9) having an O.D.=1.2 mm is seated in fluid ferrules (8) by means of a captured O-ring (5). The black polyimide on the ends of the fiber protect the Amorphous copolymers of perfluoro (2,2-dimethyl- 1,3 dioxole) and tetrafluoroethylene (e.g.Teflon AF™) beneath it from being scraped off when the fiber is inserted through the hole in the fluid ferrules. To prevent fluorophore from leaking onto the distal or proximal fiber faces and generating spurious fluorescence, the holes through which fiber assembly (7) passes through fluid ferrules (8) are sealed by means (6) of 5 Minute® epoxy. Fluid entry ports allow insertion of a needle for injection of fluids. The alignment of fiber assembly (7) and cylindrical tube (9) must be sufficiently centered with respect to one another along the longitudinal axis so as to prevent fiber assembly (7) from contacting cylindrical tube (9). Holes (4) allow sample to be brought into and out of cylindrical tube (9). Cartridges were stored at room temperature until used.

Coating (2) provides a means of mounting the sensitized fiber within the sensor cartridge which minimizes loss of light at points of contact between the fiber and the supporting parts of the cartridge and the coupling capillary. The specific coating which is utilized in the preferred embodiments is Amorphous copolymers of amorphous copolymers of perfluoro (2,2-dimethyl-1,3 dioxide) and tetrafluoroethylene (e.g.Teflon AF™), which has a refractive index of approximately 1.31. Annularizing fiber (17) also is clad with amorphous copolymers of perfluoro (2,2-dimethyl-1,3 dioxide) and tetrafluoroethylene (e.g.Teflon AF™). Appreciation of this aspect of the apparatus requires an understanding of the role played by refractive index in evanescent sensing apparatus. The sine of the maximum external half cone angle at which light can be injected into an optical waveguide so as to propagate by total internal reflection within said optical fiber is known as the numerical aperture of the waveguide (NA). The first equation given below defines the relationship between the NA of the waveguide and the refractive indices of its core and cladding. The second equation relates the refractive indices of the waveguide and its surrounding medium to the maximum external angle of a light ray that will propagate under total internal reflection within the waveguide.

$$\text{N.A.} = (\eta_{core}^2 - \eta^{2clad})^{1/2} \quad \text{Equation 9}$$

$$\text{N.A.} = \eta \sin \theta_{max} \quad \text{Equation 10}$$

where η=1 for air,
$\eta_{core}$=refractive index of the optical waveguide,
$\eta_{clad}$=refractive index of the material or sample surrounding the optical waveguide.

The refractive index of an aqueous sample is approximately 1.33. At the excitation wavelength used in the current embodiment, the refractive index of a fused silica optical fiber is approximately 1.456. From the above equation it can be calculated that light injected at a half cone angle of 36.3° will be totally internally reflected by the sensor fiber in an aqueous sample. Light at half cone angles greater than this will be lost from the fiber. The coating of refractive index 1.31 provides total internal reflection of light injected for angles less than a cone angle of 39.5°, thus an annular beam can be injected into a sensor fiber at angles at or near the critical angle for the sensor in an aqueous sample, without a loss of light. This makes possible the use of the capillary coupler shown in FIG. 5, wherein both the annularizing fiber and the sensor fiber are clad with Amorphous copolymers of amorphous copolymers of perfluoro (2,2-dimethyl-1,3 dioxide) and tetrafluoroethylene (e.g.Teflon AF™) to provide very low loss transfer of the light, annularized at optimum angle, to the sensor.

Component 4a

The Means of Positioning the Waveguide Sensor Cartridge

Figure 5:
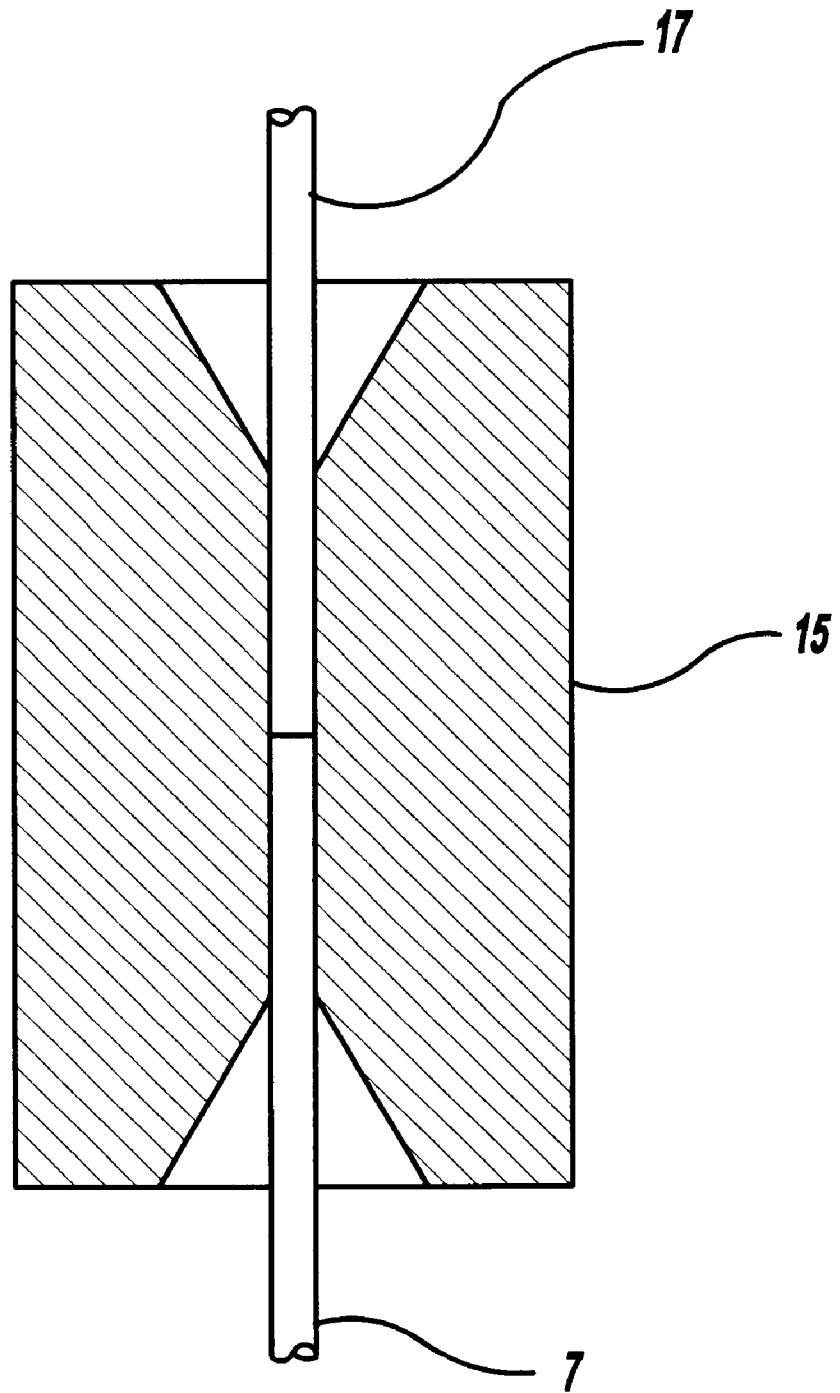
FIG. 5: Shows a front cross sectional view of the coupling capillary means by which the sensor cartridge of this invention is coupled to the annularizing fiber.
Figure 6:
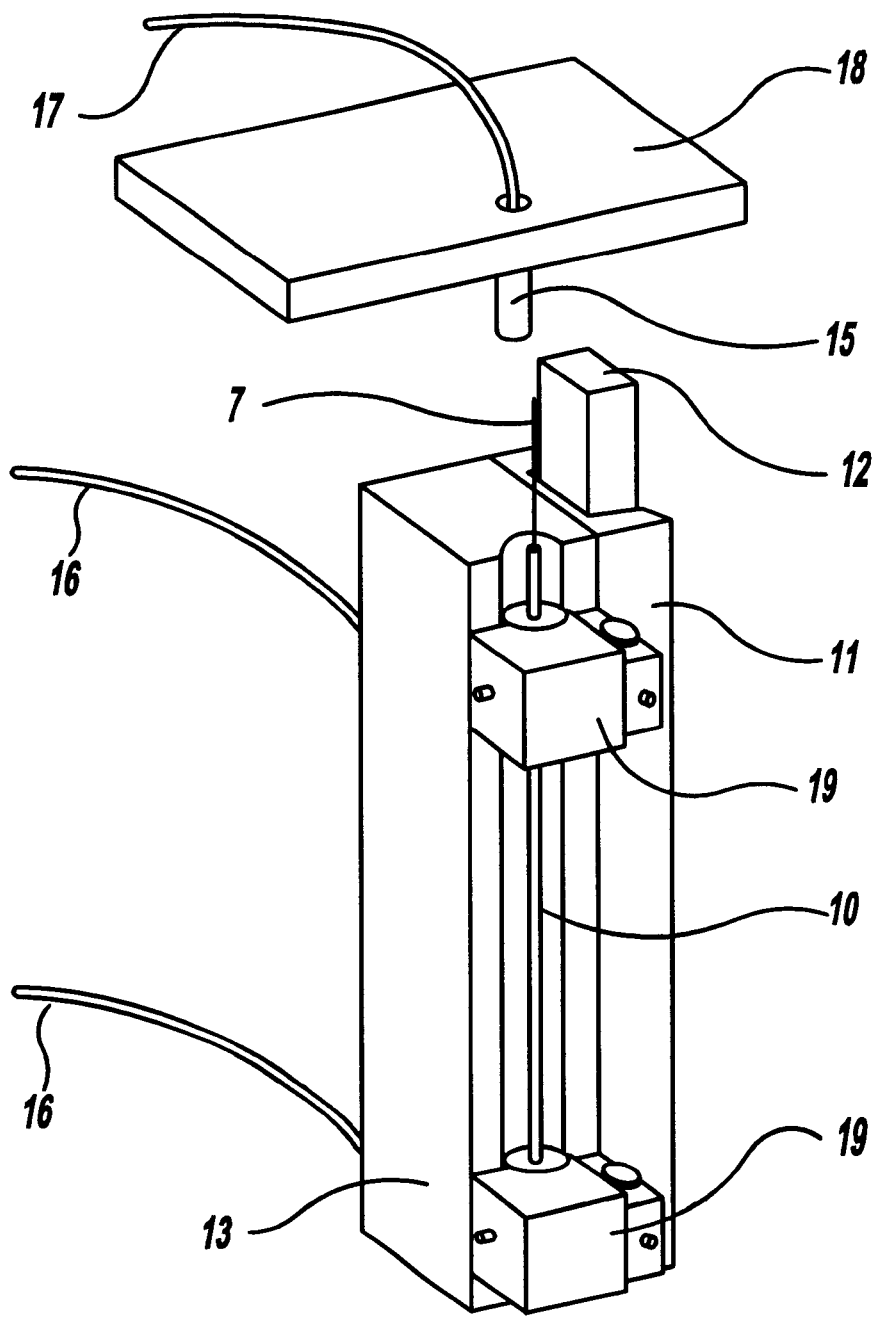
FIG. 6: Shows a positioning apparatus of this invention which provides a means by which the sensor cartridge is reliably brought into proper position in the coupling capillary.

The sensor cartridge was positioned using the apparatus shown in FIGS. 5 and 6. With reference to FIG. 5, capillary coupler (15) provides means by which annularizing fiber (17) is butt coupled to fiber assembly (7) of sensor cartridge (10). In order to minimize loss of light at the point of coupling, said coating (2) should possess a refractive index which is essentially equivalent to that of the cladding of annularizing fiber (17). Fiber assembly (7) and annularizing fiber (17) easily enter capillary coupler (15) due to beveling of the entrance holes. The diameter of the inner bore of the coupler is such that said fibers are confined in all directions so that said fibers may be precisely mated by butt coupling. The material of the coupling capillary is non-abrasive in nature so that coating (2) is not scraped off of fiber assembly (7) during positioning in capillary coupler (15).

FIG. 6 describes means by which sensor cartridge (10) may be replaced and yet each cartridge is automatically brought into the correct position with respect to coupling capillary (15). Sensor cartridge (10) is essentially positioned between two V-blocks, the first being a V formed into the front surface of positioning apparatus body (13), and the second being carved into the rear surface of hinged support (19). Hinged support (19) is fastened to positioning apparatus body (13) in a manner permitting hinged support (19) to swing away from sensor cartridge (10) in order to replace said sensor cartridge. When closed, said hinged support is anchored shut by means of a clasp. Sensor cartridge (10) is placed in positioning apparatus body (13) in a manner which causes sample inlets (16) to be pressed into holes (4) of sensor cartridge (10) in a manner which prevents leaking of sample. Positioning apparatus body (13) is mounted on a translating component (11) which slides along track (12). Track (12) is mounted on the sensor housing, as is coupling capillary support (18), in a manner such that fiber assembly (7) is brought into coupling capillary (15) when positioning apparatus body (13) is translated along track (12) in the direction of capillary coupler (15). When fiber assembly (7) has been brought into contact with annularizing fiber (17) in coupling capillary (15), a screw is tightened to hold positioning apparatus body (13) in that location. To change cartridges, said screw is loosened, positioning apparatus body (13) is translated away from coupling capillary (15) along track (12), hinged support (19) is unclasped and opened and sensor cartridge (10) is replaced.

Component 5a

A Means of Acquiring Data from the Optical Apparatus.

A MacIntosh™ Powerbook was programmed using Labview™ software from the National Instruments Company so that the laser diode is modulated on and off every 2 seconds for the first 10 seconds and every 4 seconds for the next 74 seconds and the readings from a Stanford Research Systems Model SR810 DSP lock-in amplifier are obtained using a GPIB interface card.

Component 6a

Preparation of Cy5-tagged-estrogen-receptor Solutions.

Dr. James L. Wittliff, director of the Hormone Receptor Laboratory at the James Graham Brown Cancer Center of the University of Louisville provided yeast recombinant human estrogen receptor preparations. These were produced by fusion of the receptor gene with ubiquitin with subsequent over expression in yeast under the control of the Cupi promoter as previously described in the literature in Wittliff, J. L., Dong, J., Schaupp, C., Folk, P, Butt, T. R., "Characteristics of the Human Estrogen Receptor Protein Produced in Microbial Expression Systems," Steroid Hormone Receptors: Basic and Clinical Objects, ed. V. K. Moudgil. Hormones in Health and Disease, (Boston: Birkhauser, 1993), pp. 473–501. This text is fully and completely incorporated herein by reference, word for word and paragraph for paragraph.

Expression of Human Estrogen Receptor in Yeast:

*Saccharomyces cerevisiae* strain AF103 was transformed with the YEpElO plasmid containing the ubiquitin-human estrogen receptor gene-fusion and grown in CM-Trp media with 10 mM $CuSO_4$ as described by Wittliff J. L., Dong, J., Schaupp, C., Folk, P, Butt, T. R. In V. K. Moudgil , Ed., Steroid Hormone Receptors: Basic and Clinical Objects, pp. 473–501, 1993 and in Graumann, K., Wittliff, J. L., Raffelsberger, W., Miles L., Jungbauer, A. and Butt, T. R., *Journal of Steroid Biochemistry and Molec Biol.* 57:293–300; 1996. This text is fully and completely incorporated herein by reference, word for word and paragraph for paragraph.

The yeast was grown with agitation at 30° C. in 700 ml of media using 2.8 L Fembach flasks until the OD600 nm reached 0.73–0.75 (i.e., late log phase). Induction was performed by adding CuSO4 to a final concentration of 100 mM and growing the cells for an additional 2 hours. Alternatively, untransformed yeast (*Saccharomyces cerevisiae* AF103, host strain) was grown in YPD media (Ausubel et al., Current Protocols in Molecular Biology) and harvested at an $OD_{600\ nm}$ reading of 0.90–0.93.

Cells were harvested by centrifuging the cultures for 5 minutes at 4000 g in an HS-4 rotor (Sorvall) and washed by resuspending first in 100 mM KCI and, after subsequent centrifugation, resuspending in $P_{50}$EGMo buffer (50 mM $K_2HPO_4$,1.5 mM EDTA, 10% glycerol, 10 mM $Na_2Mo_4$. pH 7.4). All of the following steps were performed on ice. Yeast pellets were resuspended in 2 pellet-volumes of freshly prepared lysis buffer containing 10 mM monothioglycerol and 1 mM PMSF. Aliquots (1.5 ml) of the suspension were pipetted into tubes containing 1.5 ml of glass beads (0.5 mm diameter). Using a Vortex mixer, the yeast cells were beaten 5 times for 30 sec and allowed to cool on ice (minimum of 30 sec) between each round of agitation to extract the receptor protein. A hole was punched in the bottom of each tube and the extract was drained into a 2 ml tube and centrifuged 1100 g at 4° C. in, a Beckman TJ6 centrifuge. Supernatants were collected for preparation by ultracentrifugation. Pellets of unbroken yeast cells were resuspended in lysis buffer and extracted again.

The supernatants from the low speed separation step were centrifuged in a Beckman L8-M ultracentrifuge using a 50.2 rotor for 30 minutes at 100,000 g. After centrifugation, the supernatants were removed, avoiding the lipid layer on the surface. The protein concentration was determined using the Biorad reagent (Hercules, Calif.) with the Bradford assay. Receptor binding capacity was measured by association with radio-labeled estradiol-17 β in the presence and absence of unlabeled diethylstilbestrol and analyzed by the One-Site® program (Lundon Software, Inc.). Receptor content was measured by enzyme immunoassay using a sandwich-type procedure. Integrity and size of the human recombinant, estrogen receptor was evaluated by Western blot analysis using a variety of monoclonal antibodies. These preparations were used for subsequent purification steps.

Cy5-Tagging of Recombinant Human Estrogen Receptor

Buffer content and conditions of yeast extracts containing estrogen receptor were changed using open column chromatography with Sephadex 100 as the stationary phase and 0.1 M potassium carbonate buffer at pH 9.3 containing 1.5 mM EDTA, 10 mM molybdate, and 10% glycerol as mobile phase. The eluent was collected as 1.2 ml fractions and the protein content was measured using a Bradford protein assay. The first 15–20 fractions contained the high molecular weight proteins including the 65 kDa human estrogen receptor. Fractions exhibiting receptor activity were pooled and incubated with the content of 1 vial Cy5 fluorescent dye (Amersham, Arlington Heights, Ill.) for 2 hours at −4° C. To stop the reaction, an equal volume of $P_{50}EGM$ buffer, pH 6.5, containing 1 mg/ml casein was added, aliquoted into smaller volumes, and frozen at −80° C. In certain experiments the ligand binding activity of the Cy5-tagged preparations were determined to evaluate the influence of the dye.

Purification of Human Recombinant Estrogen Receptor by HLPC

Estrogen receptor proteins in yeast extracts were first partially purified by size exclusion chromatography using Sephacryl S 300 (Sigma, St. Louis, Mo.) as the stationary phase and $P_{50}EGMo$ buffer (50 mM $K_2HPO_4$ buffer, pH 7.4 containing 1.5 mM EDTA, 10% glycerol, 10 mM $Na_2Mo_4$) with 100 mM KCl as mobile phase. The eluent was collected as 1.2 ml fractions and the protein content of each was measured using a Bradford protein assay. Analysis of the protein concentrations of the various fractions revealed two major peaks with variable quantities of estrogen receptor activity. The fractions representing the higher molecular weight peak were pooled and an equal volume 3.8 M ammonium sulfate was added just prior to injection in a Beckman HPLC unit. Synchropako Propyl-300 hydrophobic interaction chromatography column (SynChrom, Inc., Lafayette, Ind.) was used as the stationary phase and elution was performed with a gradient of ammonium sulfate ranging from 2.0–0.0 M in $P_{50}EGMo$ buffer at pH 7.4. Sample aliquots were evaluated using the Bradford protein assay. Western blotting and ELISA were used to determine the fractions containing human estrogen receptor. These active receptor preparations were pooled, used in certain labeling experiments or immediately frozen on dry ice and stored.

This receptor preparation is sufficiently stable to permit its use in the 15 minute room temperature protocol employed in obtaining fiber optic sensor data. The preparation was shown to exhibit hormone binding characteristics similar to those of the wild type receptor including ligand affinity ($K_d$ value= $10^{-10}$–$10^{-11}$ for estradiol-17β) and specificity (affinity constants and competitive behavior of a variety of naturally occurring estrogens and therapeutic estrogen mimics similar to wild type receptor). The yeast preparation, which contained 1 μg of hER protein per mg of total protein, was diluted with 50 mM phosphate buffer pH 7.5, containing 10% glycerol, 500 mM KCl, 2 mM dithiothreitol, 1 mM EDTA, 1 mM sodium vanadate, 0.02% sodium azide (hereafter referred to as "receptor buffer") to give a total receptor concentration of $1.1 \times 10^{-10}$M.

This solution comprised said calibration standard of component 6a. The other proteins in the yeast preparation included heat shock proteins which stabilized the hER in solution. This receptor preparation was used as the calibration solution. Immediately after preparation it was pipetted in 135 μl aliquots into microcentrifuge tubes, snap frozen and stored at −80° C. They were not thawed again until they were used with the fiber sensor. Sample solutions of component 6a were similarly prepared, except that the dilution at the end with receptor buffer gave a total receptor concentration of $4.4 \times 10^{-10}$M. If the solution was to be used with an ERE fiber (component 1a type 2), then polydeoxyinosinic-deoxycytidylic acid sodium salt was added to the receptor buffer to prevent nonspecific binding to the ERE fiber. Solutions containing $4.4 \times 10^{-10}$M Cy5-tagged-estrogen-receptor solution and in addition to a pre-determined amount of estrogen or estrogen mimic were created to test the impact of said estrogen or estrogen mimic.

Aliquots of 135 μl of both calibration standard or sample receptor solutions having no added ligand were pipetted into microcentrifuge tubes and frozen. Immediately upon thawing, to each 135 μl of sample solution was added 15 μl of a concentration of the test compound so as to bring the final concentration of test compound in the aliquot to either OM, $2\times 10^{-10}$ M, $7\times 10$–$10$ M, $2\times 10^{-9}$ M, $7\times 10^{-9}$ M, $2\times 10^{-8}$ M, $7\times 10^{-8}$ M, $2\times 10^{-7}$ M, $2\times 10^{-7}$ m or $2\times 10^{-6}$M.

Component 7a

Preparation of Solution of Cy5 Fluorophore for Measuring Scatter Background from the Calibration and Sample Solutions.

Cy5 which had not coupled to the receptor and which was recovered as the component passing through a Centricon 30 concentrator after a protein had been tagged with Cy5, was diluted with receptor buffer so that it gave an absorbance at 650 nm equivalent to that of component calibration standards or sample solutions. These solutions were used to evaluate scatter background from the sensor during measurements.

Method of Utilizing the First Preferred Embodiment to Identify Estrogen Mimics

All fiber sensors were subjected to identical protocol comprised of:
1) The sensor cartridge was mounted in the positioning apparatus and focused so that light from the laser diode enters the fiber at or near the critical angle.
2) A solution of 1% casein was injected into the sensor.
3) Sensor background was measured.
4) An aliquot of calibration standard and an aliquot of sample solution were removed from the freezer and thawed at 23° C. 15 μl of test sample was added to the sample solution aliquot and mixed gently with a vortex to constitute a test sample solution.
5) Exactly ten minutes after the samples were removed from the freezer, the casein solution was removed and 150 μl of calibration scatter standard was drawn into the sensor and a reading taken.
6) Calibration scatter standard was removed from the sensor and 150 μl of the sample scatter standard was drawn into the sensor and a reading taken.
7) The sample scatter standard was removed from the sensor and 150 μl of the aliquot of calibration standard was drawn into the sensor and automatic data acquisition begun.
8) 84 seconds later the aliquot of component 2a was removed and the aliquot of the test sample solution was drawn into the sensor and automatic data collection continued for another 84 seconds.
9) 84 seconds later the aliquot of the test sample solution was removed and receptor buffer was drawn into the sensor and automatic data collection continued for another 10 minutes.
10 The quantities S/C were calculated for each test sample as described in step 9m procedure 1.

11) The concentrations at which the peaks occurred for estradiol and for the other test compound (diethylstilbestrol and tamoxiphen) were compared. Estradiol is known to have a $K_d$ of roughly $1.1 \times 10^{10}$ M for the receptor. From this knowledge it can be calculated from Equation 8, that within the level of accuracy permitted by the choice of standards $$K_d(DES) = K_d(estradiol) * (2 \times 10^{-8})/(2 \times 10^{-9}) = 1.1 \times 10^{-9} M.$$

This is as close to the value of $K_d$ for DES, which is $1.8 \times 10^{-9}$ M, obtained by conventional methods, as can be expected from the choice of concentrations. The smaller the interval between choices of concentrations, the more accurately $K_d$ can be measured.

Figure 7:
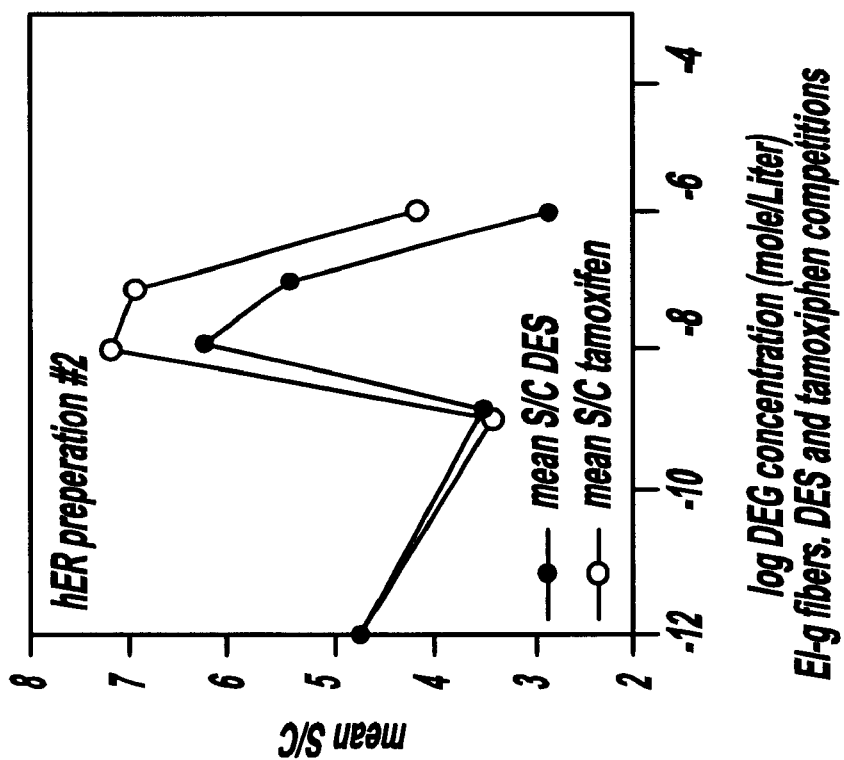
FIG. 7: Shows data obtained using the apparatus and means of this invention to assess the effects of estradiol-17β, diethylstilbestrol and tamoxifen on binding between human estrogen receptor and a sensor cartridge containing an estrone-3-glucuronide optical fiber.
Figure 7:
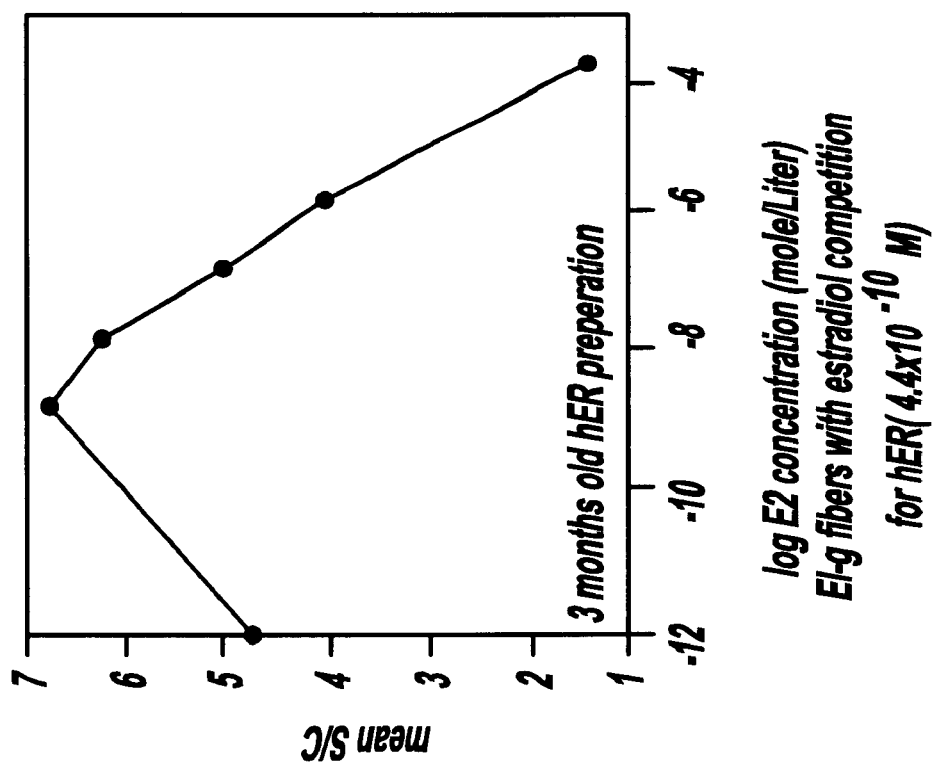

Data obtained in this manner is shown in FIG. 7.

12) Using fiber sensors of component 1a type 2, and the foregoing procedure the S/C value was calculated for several different estrogens tested at $10^{-6}$M concentration. Results shown in the table below demonstrate good agreement between the known biological activity of the compound tested and the S/C value obtained for that compound using the ERE type fibers. 17β-estradiol, the strongest biological estrogen increases binding to the ERE fiber by the greatest amount. Diethylstilbestrol and zearalenone, two estrogen mimics increase binding to the ERE more than do the weak biological estrogens, estrone and estriol. Tamoxiphen, which acts as an antiestrogen, binds to the receptor as shown in the graph above, but does not increase binding to the ERE. This is reasonable in view of its anti-estrogenic activity. Thus the combined data from the estrone-3-glucuronide fiber and the ERE fiber can be used to predict the likely biological impact of the tested compound on estrogen-mediated processes. Results are shown in the following table.

| Compound | Response of ERE fiber to hER and $10^{-6}$M compound (control = 3.51) | Type of bioactivity |
|---|---|---|
| 17β-estradiol | 7.08 | strong natural estrogen |
| estrone | 4.44 | weak natural estrogen |
| estriol | 4.25 | weak natural estrogen |
| diethylstilbestrol | 4.87 | strong synthetic estrogen |
| zearalenone | 5.01 | synthetic estrogen |
| tamoxifen | 3.35 | synthetic anti-estrogen |

The Second Example of a Ppreferred Embodiment

The Second Preferred Embodiment of the present invention utilizes components adapted to measurement of estrogen receptor in a tumor tissue biopsy sample to assess the probable impact of tamoxifen on the cancer represented by that sample. In this embodiment, the procedures and components of the apparatus are similar to those of the first embodiment with the addition of a type 3 fiber sensor and other changes which are described below.

Component 1a, type 2

Preparation of Fibers Having an ERE Surface Feature.

These fibers are prepared as described under the first preferred embodiment of this invention.

Component 1a, type 3

Preparation of Fibers Having an Anti-Estrogen Receptor Surface.

Optical fibers were created as described under component 1a type 1 up through the addition and removal of GMBS. At this point anti-estrogen receptor antibody such as ER1D5, obtained from Immunotech, Inc., Westbrook, Me., was diluted to a concentration of 0.05 mg per ml and the solution is injected into the fiber processor for 2 hours at room temperature. Fibers are washed and mounted in sensor cells as previously described.

Component 6a type 2

Preparation of Cy5-tagged Anti-Estrogen Receptor Solutions.

The recombinant estrogen receptor described in preferred embodiment #1 is used as a control sample. The sample being tested is prepared from frozen tissue biopsy by homogenization in the previously described buffer followed by centrifugation to yield a cytosol extract These methods are known to those skilled in the art of tissue biopsy preparation. The cytosol is incubated for 10–60 minutes in the presence of Cy5-tagged anti-receptor antibody. Antibody is chosen so that it does not interfere with either ligand binding or binding to the ERE.

Dilutions of the anti-endocrine agent which is being tested as a possible treatment for the cancer represented by the sample being tested are added to samples of tissue biopsy extract. This preparation is then used in the context of sensors containing component 1a type 2 and 1a type 3 according to the procedures described for the first embodiment and data is processed by taking calculations as far as determination of S/C without the anti-endocrine compound and in the presence of various dilutions of the said compound. The data from sensors containing component 1a type 3 will confirm the estrogen-positive status necessary for anti-endocrine therapy to be a reasonable option. Significant reduction of the value of S/C from the sensor containing component 1a type 2 in the presence of the anti-endocrine compound A compound shows a good likelihood that said compound will be an effective treatment for the cancer represented by the sample. In cases where resistance to treatment has developed, the S/C value will be expected to rise back from its previously suppressed value unless the suppression results from a mutation in the estrogen response element.

What is claimed is:

1. An apparatus for determining the binding affinity between a pair of molecular species where one molecular species comprises at least a portion of a biological receptor such that said portion has binding affinity for a second molecular species, wherein said receptor is not an antibody, said apparatus comprising:

(a) a light source which generates and transmits a light signal, (b) an optical waveguide which receives said transmitted light signal in which an evanescent field is generated;

(c) a plurality of molecules of one member of said pair said molecules being affixed to a lateral surface of said optical waveguide;

(d) a molecular tag attached to molecules of one member of said pair, said tag interacting with said evanescent field so that when a complex forms between members of the pair, the characteristics of said light signal propagating within said optical waveguide are altered; and (e) annularizing, detection and processing means, connected to said waveguide for kinetic monitoring of said characteristics of said light signal propagating within the optical waveguide.

2. The apparatus of claim 1 wherein said receptor comprises estrogen receptor.

3. The apparatus of claim 2 wherein said optical waveguide includes estrogenic molecules affixed to its surface.

4. The apparatus of claim 1 wherein said optical waveguide includes, affixed to its surface, a nucleotide sequence to which said receptor binds.

5. The apparatus of claim 4 wherein said nucleotide sequence binds to estrogen receptor.

6. The apparatus of claim 4 wherein said nucleotide binds to progesterone receptor.

7. The apparatus of claim 1 wherein said optical waveguide comprises an optical fiber.

8. The apparatus of claim 1 wherein said receptor further comprises a molecular tag which is an enzyme capable of acting upon a substrate so as to produce a chemical substance which when bound to said optical waveguide, produces an alteration in a certain characteristic of light collected from said waveguide.

9. The apparatus of claim 1 wherein said receptor comprises progesterone receptor.

10. The apparatus of claim 9 wherein said optical waveguide has progestinic molecules affixed to its surface.

11. The apparatus of claim 1 wherein said receptor comprises testosterone receptor.

12. The apparatus of claim 11 wherein said optical waveguide has androgenic molecules affixed to its surface.

13. The apparatus of claim 12 wherein said nucleotide sequence binds to androgen receptor.

14. The apparatus of claim 1 wherein said molecular tag selected from the group consisting of fluorescent, phosphorescent and luminescent molecules.

15. The apparatus of claim 1 wherein the member of said pair which is affixed to said waveguide possesses a fluorescent molecular tag which, when excited by said evanescent field emits light at a wavelength which stimulates fluorescence in a second molecular tag attached to the other member of said pair.

16. The apparatus of claim 1 wherein the receptor is affixed to the surface of the optical waveguide and a partner possesses said molecular tag.

17. An apparatus for measuring the effect of a first molecular species on binding between a second and third molecular species said apparatus comprising:

(a) a light source which generates and transmits a light signal;

(b) an optical waveguide which receives said transmitted light signal in which an evanescent field is generated;

(c) a plurality of molecules of said second molecular species being affixed to a lateral surface of said optical waveguide;

(d) a molecular tag attached to molecules of said third molecular species, said tag interacting with said evanescent field so that when a complex forms between said second and third molecular species, the characteristics of said light signal propagating within said optical waveguide are altered;

(e) solutions containing said first molecular species; and, (f) annularizing, detection and processing means, connected to said waveguide for providing kinetic monitoring of said characteristics of said light signal propagating within the optical waveguide.

18. An apparatus of claim 17 wherein said second molecular species is a nucleotide sequence and said third molecular species is a biological receptor, where said receptor is not an antibody.

19. An apparatus of claim 17 wherein said second molecular species is an accessory molecule of a biological signal transduction complex and said third molecular species is a biological receptor, where said receptor is not an antibody.

20. An apparatus of claim 17 wherein said second molecular species is a biological receptor, where said receptor is not an antibody, and said third molecular species is a nucleotide sequence.

* * * * *